(12) United States Patent
Corbeau et al.

(10) Patent No.: US 6,200,811 B1
(45) Date of Patent: *Mar. 13, 2001

(54) CELL TRANSFORMATION VECTOR COMPRISING AN HIV-2 PACKAGING SITE NUCLEIC ACID AND AN HIV-1 GAG PROTEIN

(75) Inventors: Pierre Corbeau, Montpellier (FR); Gunter Kraus, Miami, FL (US); Flossie Wong-Staal, San Diego, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/822,516

(22) Filed: Mar. 24, 1997

Related U.S. Application Data

(60) Provisional application No. 60/015,555, filed on Apr. 2, 1996.

(51) Int. Cl.[7] .............................. C12N 15/86; C12N 7/01; C12N 15/70
(52) U.S. Cl. .................. 435/456; 435/320.1; 435/235.1; 435/440; 435/455
(58) Field of Search .............................. 435/320.1, 172.3, 435/235.1, 440, 455, 456; 514/44; 536/24.1

(56) References Cited

U.S. PATENT DOCUMENTS

| | | | |
|---|---|---|---|
| 5,723,333 | * 3/1998 | Levine et al. | 435/325 |
| 5,811,275 | * 9/1998 | Wong-Staal et al. | 435/455 |
| 5,861,282 | 1/1999 | Aldovini et al. | 435/69.3 |
| 5,883,081 | 3/1999 | Kraus et al. | 514/44 |

FOREIGN PATENT DOCUMENTS

WO 97/36481   10/1997   (WO) .

OTHER PUBLICATIONS

Buchschacher et al. Human Immunodeficiency Virus Vectors for Inducible Expression of Foreign Genes. J. of Virol., vol. 66, No. 5, pp. 2731–2739, May 1992.*

Levy, J. A. Pathogenesis of Human Immunodeficiency Virus Infection. Microbiological Reviews, vol. 57, No. 1, pp. 183–289, Mar. 1993.*

Crystal, R. G. Transfer of Genes to Humans: Early Lessons and Obstacles to Success. Science, vol. 270, pp. 404–410, Oct. 20, 1995.*

Johnston et al. Present Status and Future Prospects for HIV Therapies. Science, vol. 260, pp. 1286–1293, May 28, 1993.*

Orkin et al. Report and Recommendations of the Panel to Assess the NIH Investment in Research on Gene Therapy. Distributed by the National Institutes of Health, Bethesda MD. Obtained from www.nih.gov., Dec. 7, 1995.*

Richardson, et al., Packaging of Human Immunodeficiency Virus Type 1 RNA Requires cis–Acting Sequences outside the 5' Leader Region, Jul. 1993, Journal of Virology, pp. 3997–4005.

Lori, et al., Effect of Reciprocal Complementation of Two Detective Human Immunodeficiency Virus Type 1 (HIV–1) Molecular Clones on HIV–1 Cell Tropism and Virulence, Sep. 1992, Journal of Virology, pp. 5553–5560.

Rizvi, et al., Simian Immunodeficiency Virus RNA is Efficiently Encapsidated by Human Immunodeficiency Virus Type 1 Particles, May 1993, Journal of Virology, pp. 2681–2688.

Shimada, et al., Targeted and Highly Efficient Gene Transfer into CD4+ Cells by a Recombinant Human Immunodeficiency Virus Retroviral Vector, Sep. 1991, The Journal of Clinical Investigation, Inc., vol. 88, pp. 1043–1047.

Carroll, et al., A Human Immunodeficiency Virus Type 1 (HIV–1)–Based Retroviral Vector System Utilizing Stable HIV–1 Packaging Cell lines, Sep. 1994, Journal of Virology, pp. 6047–6051.

Clever, et al., RNA Secondary Structure and Binding Sites for gag Gene Products in the 5' Packaging Signal of Human Immunodeficiency Virus Type 1, Apr. 1995, Journal of Virology, pp. 2101–2109.

Aldovini, et al., Mutations of RNA and Protein Sequences Involved in Human Immunodeficiency Virus Type 1 Packaging Result in Production of Noninfectious Virus, May 1990, Journal of Virology, pp. 1920–1926.

* cited by examiner

Primary Examiner—Deborah J. Clark
(74) Attorney, Agent, or Firm—Townsend and Townsend and Crew LLP

(57) ABSTRACT

By transducing cells with an HIV-1-MN molecular clone deleted in the major packaging sequence, a stable HIV-1 packaging cell line, $\psi 422$ was produced. $\psi 422$ cells form syncytia with CD4 positive cells, correctly express HIV-1 structural proteins, and produce large amount of mature particles with normal RT activity. These particles are not infectious. When stably transfected with an HIV-based retroviral vector, the $\psi 422$ cell line produces hybrid virions capable of transducing CD4 positive cells with high efficiency (e.g., $10^5$ cells/ml). The availability of this stable, noninfectious HIV-1 packaging cell line capable of generating high titer HIV vectors enables the use of HIV-1 based nucleic acids delivery systems, for example, in gene therapy. An HIV-2 based vector is packaged by the packaging cell lines, demonstrating that HIV-2 cell transformation vectors are packaged by the packaging cell line. HIV based vectors packaged by the high efficiency cell lines are shown to have anti-HIV activity per se.

41 Claims, 7 Drawing Sheets

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 57 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

GGTGAGTACG TACGCCAAAA ATTCTTGACT AGCGGAGGCT AGAAGGAGAG AGCCATG      57

(2) INFORMATION FOR SEQ ID NO:2:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: RNA (xi) SEQUENCE DESCRIPTION: SEQ ID NO:2:

NNNSNGUCNN NNNNNN      16

(2) INFORMATION FOR SEQ ID NO:3:

(i) SEQUENCE CHARACTERISTICS:
      (A) LENGTH: 21 base pairs
      (B) TYPE: nucleic acid
      (C) STRANDEDNESS: single (D) TOPOLOGY: linear (ii) MOLECULE TYPE: DNA (xi) SEQUENCE DESCRIPTION: SEQ ID NO:3:

TGGATGGGTT AATTTACTCC C                                                      21

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

GGCGCGCCTC ACCAGTCGCC GCCCC                                                  25

(2) INFORMATION FOR SEQ ID NO:5:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

GGGGCGCGCC GAGAGAGATG GGGTGCGAGA GCGTCGG                                     37

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

CTGATCATAC TGTCTTACTT TG                                                     22

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

CCGCTCGAGA TGAGCGAAAA ATACATCGTC                                             30

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

CGGTCGACTT AGCGGCCGCG ACCGGAGATT GGCGGG                                          36

(2) INFORMATION FOR SEQ ID NO:9:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

TTTTCGCGAG CGGCCGCCGG AAGGGCTAAT TCACTCC                                         37

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

GGTATCTTTC CACAGCTAGG                                                            20

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

GGAGCTTTGT TCCTTGGG                                                              18

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

ATCAACCAGC GGACGACCAG                                                            20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

AGCTACGATC ACGACAACCA                                                            20

(2) INFORMATION FOR SEQ ID NO:14:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

TTTTCGCGAG CGGCCGCTGC TAGAGATTTC CACACTG        37

CELL TRANSFORMATION VECTOR COMPRISING AN HIV-2 PACKAGING SITE NUCLEIC ACID AND AN HIV-1 GAG PROTEIN

CROSS REFERENCE TO RELATED APPLICATIONS

This application is a continuation-in-part of U.S. provisional patent application U.S. Ser. No. 60/015,555, by Corbeau et al., filed Apr. 2, 1996, which is incorporated herein by reference for all purposes.

BACKGROUND OF THE INVENTION

The primate lentiviruses human immunodeficiency virus (HIV) type 1 (HIV-1), and type 2 (HIV-2) cause the disease AIDS, and are epidemic in human populations world wide. HIV-1 and HIV-2 are genetically related, antigenically cross reactive, and share a common cellular receptor (CD4). See, Rosenburg and Fauci (1993) in *Fundamental Immunology, Third Edition* Paul (ed) Raven Press, Ltd., New York (Rosenburg and Fauci 1) and the references therein for an overview of HIV infection.

The surface glycoprotein CD4 is found mainly on a subset of T cells, monocytes, macrophage and some brain cells. HIV has a lipid envelope with viral antigens that bind the CD4 receptor, causing fusion of the viral membrane and the target cell membrane and release of the HIV capsid into the cytosol. HIV corrupts the cellular machinery of infected cells by causing the cell to replicate copies of the HIV virus, and eventually death of infected immune cells, thereby disabling the immune system and killing the patient due to complications associated with a disabled immune system. HIV infection also spreads directly from cell to cell, without an intermediate viral stage. During cell-cell transfer of HIV, a large amount of viral glycoprotein is expressed on the surface of an infected cell, which binds CD4 receptors on uninfected cells, causing cellular fusion. This typically produces an abnormal multinucleate syncytial cell in which HIV is replicated and normal cell functions are suppressed.

Due to the pandemic spread of HIV, an intense worldwide effort to unravel the molecular mechanisms and life cycle of these viruses is underway. It is now clear that the life cycle of these viruses provides many potential targets for inhibition by gene therapy, including cellular expression of transdominant mutant gag and env nucleic acids to interfere with virus entry, TAR (the binding site for tat, which is typically required for transactivation) decoys to inhibit transcription and trans activation, and RRE (the binding site for Rev; i.e., the Rev Response Element) decoys and transdominant Rev mutants to inhibit RNA processing. See, Wong-Staal et al., PCT/US94/05700, and Rosenburg and Fauci (1993) in *Fundamental Immunology, Third Edition* Paul (ed) Raven Press, Ltd., New York and the references therein for an overview of HIV infection and the HIV life cycle. Gene therapy vectors utilizing ribozymes, antisense molecules, decoy genes, transdominant genes and suicide genes, including retroviruses are found in Wong-Staal et al., id, and Yu et al., *Gene Therapy* (1994) 1:13–26. Antisense and ribozyme therapeutic agents are of increasing importance in the treatment and prevention of HIV infection.

In previous studies, the efficacy of several anti-HIV-1 hairpin ribozymes in inhibiting virus replication in human T cell lines was demonstrated. See, Wong-Staal et al., PCT/US94/05700; Yamada et al., *Virology* (1994) 205:121–126; Yamada et al., *Gene Therapy* (1994) 1:38–45; Yu et al., *Proc Natl. Acad. Sci. USA* (1993) 90:6340–6344, and Yu et al., *Virology* (1995) 206:381–386. With an anti-U5 ribozyme which targets a highly conserved region of the HIV-1 genome, it was shown that intracellular immunization of primary lymphocytes or hematopoietic progenitor cells lead to resistance of both lymphotropic and macrophage tropic HIV-1 strains (Leavitt et al., *Hum. Gene Ther.* (1994) 5:1115–1120; Yu et al., *Proc. Natl. Acad. Sci. USA* (1995) 92:699–703).

Recent studies of the dynamics of HIV replication in patients under antiviral therapy have reaffirmed the central role of the virus in disease progression, and provided a strong rationale for the development of effective, long term antiviral therapy (Coffin, J. M. *Science* (1995) 267:483–489; Ho et al., *Nature* (1995) 373:123–6; Wei et al., *Nature* (1995) 373:117–22). One interesting parameter from these studies is the extremely short life span of an HIV-1 infected $CD4^+$ lymphocyte (half life=1–2 days), contrasting data from other studies which gave an estimated lifespan of months to years for uninfected lymphocytes (Bordignon et al., *Hum Gene Ther.* (1993) 4:513–20). These observations are relevant for antiviral gene therapy, because a cell resistant to viral infection, or which suppresses viral replication are strongly selected for in vivo.

Gene therapeutic approaches are hampered by the limitations of the delivery systems currently used in gene therapy. For instance, the extensively used murine retroviral vectors transduce human peripheral blood lymphocytes poorly, and fail to transduce non-dividing cells such as monocytes/macrophages, which are known to be reservoirs for HIV. An appealing alternative would be to utilize HIV-based delivery systems, which would ensure optimal cell targeting and intracellular co-localization of HIV and anti-HIV therapeutics.

Gene therapeutics can target, inter alia, viral RNAs (e.g., using ribozymes, or antisense RNA), viral proteins (RNA decoys, transdominant viral proteins, intracellular single chain antibodies, soluble CD4), infectible cells (suicide genes), or the immune system (in vivo immunization). However, these various gene therapeutic approaches are hampered by the limitations of the delivery systems currently used in gene therapy. For instance, with regard to HIV treatment, the extensively used murine retroviral vectors transduce (transfer nucleic acids into) human peripheral blood lymphocytes poorly, and fail to transduce non-dividing cells such as monocytes/macrophages, which are known to be reservoirs for HIV. An appealing alternative basis for gene therapy vectors would be to utilize HIV-based delivery systems, which would ensure optimal $CD4^+$ cell targeting and intracellular co-localization of HIV target and gene therapeutic effector molecules. In addition, HIV-derived vectors could be packaged by the wild type virions of patients in vivo and thereby be replicated and disseminated to a larger pool of potentially HIV-infectible cells upon infection by HIV.

Finally, HIV cell transformation vectors are particularly desirable because of their ability to be pseudotyped to infect non-dividing hematopoietic stem cells ($CD34^+$). These stem cells differentiate into a variety of immune cells, including $CD4^+$ cells which are the primary targets for HIV infection. $CD34^+$ cells are the most important target cells for ex vivo gene therapy, because these cells differentiate into many different cell types, and because the cells are capable of re-engraftment into a patient undergoing ex vivo therapy.

Most of the previously reported HIV packaging systems have very low titers, ranging from $10^0$ to $10^2$ transducing units per ml (TU/ml), and/or result from transient transfections, which are unstable (Buchschacher, et al. (1992) *J. Virol.* 66(5):2731–2739; Rizvi, et al. (1993) *J. Virol.* 67(5):2681–2688; Carroll, et al. (1994) *J. Virol.* 68(9):6047–6051; Parolin, et al. (1994) *J. Virol.* 68(6):3888–3895; Shimada, et al. (1991) *J. Clin. Invest.* 88:10431047). A group reported a transduction efficiency of $2 \times 10^4$ TU/ml, but in this study the packaging system was infectious wild type HIV-1 (Richardson, et al. (1993) *J. Virol.* 67(7):3997–4005), which is of little practical value. The only study describing a stable cell line doubly transfected with the packaging plasmid and the vector reported transduction lower than $10^2$ TU/ml (Carroll, et al. (1994) *J. Virol.* 68(9):6047–6051).

Thus, the efforts to develop HIV-based delivery systems have so far resulted in extremely low transduction efficiencies for HIV-based vectors (Buchschacher, et al. (1992) *J. Virol.* 66(5):2731–2739; Richardson, et al. (1993) *J. Virol.* 67(7):3997–4005; Rizvi, et al. (1993) i J. Virol. 67(5):2681–2688; Carroll, et al. (1994) *J. Virol.* 68(9):6047–6051), rendering the use of HIV delivery systems impractical. This invention overcomes these and other problems. In addition, it is discovered that the regulatory elements which are used in HIV vectors (e.g. TAR, RRE and packaging signal sequences) are themselves antagonistic to HIV replication, thereby providing a level of HIV inhibition.

SUMMARY OF THE INVENTION

The invention derives from the discovery of vectors and cell lines which provide efficient packaging of HIV-packageable nucleic acids, useful, inter alia as gene therapeutic agents. A variety of packaging vectors and stable non-infectious HIV packaging cell lines are provided, with typical packaging titers of $10^4$ to $10^6$ transducing units per ml, enabling efficient transduction of $CD4^+$ cells with HIV-based gene therapy vectors. Thus, this invention provides for the making and use of packaged HIV-packageable nucleic acids for the transduction of $CD4^+$ cells, including the use of HIV-packageable nucleic acids as gene therapy vectors.

In one class of embodiments, a high efficiency packaging vector comprising a high efficiency packaging vector nucleic acid or nucleic acids is provided. In addition to the packaging nucleic acid, a packaging vector optionally includes additional components such as proteins, lipids and carbohydrates which are optionally arranged to facilitate delivery of the packaging vector nucleic acid into a cell. For instance, the packaging vector optionally comprises a viral particle surrounding the nucleic acid. Thus, the packaging vector may be a nucleic acid, e.g., a plasmid, or a nucleic acid with associated material such as a nucleic acid encapsulated in a viral delivery capsid (i.e., a viral vector unrelated to HIV, such as adeno virus, adeno-associated virus, pox virus, or the like).

The high efficiency packaging vector nucleic acid of the vector encode some or all of the proteins needed to produce an HIV-1 particle. Typically, packaging vector nucleic acids are derived from an HIV viral genome, or a portion thereof. Packaging vector nucleic acids lack the nucleic acids necessary for packaging of an RNA corresponding to the packaging vector nucleic acid into an HIV capsid. That is, packaging vector nucleic acids are not themselves encapsulated in the HIV particles which they encode, i.e., the high efficiency packaging vector nucleic acids are not themselves infective. Typically, nucleic acids corresponding to one or more, and preferably two or more, stem loops of the $\Psi$ structure are deleted or altered in the packaging vector relative to the wild-type HIV genomic RNA nucleic acid.

The particles encoded by the high efficiency packaging vector nucleic acids of the invention typically package the packaging vector nucleic acid at a level less than 10%, and more typically less than 1%, of the level that they package a nucleic acid which has a wild-type HIV packaging site. The level of nucleic acid incorporation is optionally, and typically, measured by RT-PCR. The nucleic acid preferably encodes the accessory gene vpr. In one preferred embodiment, the packaging vector nucleic acid is derived from an HIV-1-MN genomic clone, e.g., by standard cloning or mutagenesis techniques. For example, the plasmid $\Delta\Psi$ is an example preferred HIV-1-MN derived packaging vector.

Many promoters are useful in the high efficiency packaging vector nucleic acid, including known inducible and constitutive promoters. One preferred promoter comprises the 5' HIV LTR, which is induced, inter alia, in response to HIV infection. Where the packaging vector nucleic acid comprises an HIV LTR, the vector typically includes a deletion in the HIV packaging site located between the 5' LTR and the GAG gene as compared to a wild-type HIV virus.

In one preferred embodiment, the vector comprises only a portion of the nucleic acids which encode components used to make an HIV particle. Although it is possible to place all of the sequences necessary for generating HIV capsids in a single packaging vector nucleic acid, placing the sequences in multiple discreet packaging vectors increases the safety of any packaging cell line created using a packaging vector or packaging vectors. This is because there is a lowered probability of recombination events between the packaging vector nucleic acids and any HIV-packageable nucleic acid which is present in a packaging cell inadvertently resulting in an infective virus.

A high efficiency packaging vector nucleic acid, when transfected into a cell, renders the cell competent to package HIV packageable RNA at a titre of at least about $10^4$ transducing units per ml (TU), and often about $10^5$ to $10^6$ TU. A preferred packaging cell type stably transformed by the packaging vector is the Hela cell line.

When expressed in a cell, the particle encoded by packaging vector nucleic acid(s) comprises reverse transcriptase activity. Because the particles do not package packaging vector RNA, the particles are typically non-infectious. However, if expressed in a cell which also expresses wild-type genomic HIV RNA, the particles package the wild type HIV RNA, resulting in an infective HIV virus. One advantage of an HIV-based anti-HIV vector is that the vector nucleic acid is packaged by wild-type HIV during infection of a cell and disseminated to other cells in conjunction with the infecting HIV virus.

In certain preferred embodiments where the high efficiency packaging vector nucleic acid is derived from an HIV-1-MN genomic clone, nucleic acids encoded by the high efficiency packaging vector hybridize to nucleic acids encoded by an HIV-1-MN clone under stringent hybridization and wash conditions for the particular hybridization assay (typically a Southern or northern assay).

In one class of embodiments, a packaging vector as described above is used to transform a cell line to produce a high efficiency packaging cell line. The high efficiency packaging cell line typically produces at least about $10^4$ transducing HIV vector particles (i.e., particles containing HIV-packageable RNA) per ml, when the packaging cell line is transduced with an HIV-packageable nucleic acid. In preferred embodiments, the cell line produces at least about $10^5$ transducing HIV vector particles per ml. In more preferred embodiments, the packaging cell line produces at least about $10^6$ transducing HIV particles per ml.

The cell lines of the invention optionally comprise additional heterologous elements in addition to the packaging vector nucleic acid. For example, the incorporation of proteins into HIV-based retroviral particles can expand the host range of the viral particle. Accordingly, the cells optionally comprise such proteins, or nucleic acids encoding the proteins. The packaging cells optionally further include HIV-packageable nucleic acids.

The packaging cell lines of the invention are typically stable and non-infectious. In one preferred class of embodiments, the cell line is derived from the Hela cell line. One preferred Hela packaging cell line is the Ψ-422 cell line described herein. Thus, the invention provides both methods for making a stable packaging cell line, and cell lines produced by the methods. Supernatants from the cell lines are also provided. In preferred embodiments, the cell line is made before any HIV-packageable nucleic acid is introduced into the cell. Thus, in preferred embodiments, the packaging vector and the HIV-packageable nucleic acid are not co-transfected into a cell line. It is now discovered that separate transfection of the packaging vector and the packageable nucleic acid reduces the likelihood of a recombination event resulting in an infective HIV particle. In addition, once a cell line is stably transformed with a packaging vector, the cell line can be used to package essentially any nucleic acid which includes an HIV packaging site. Thus, transforming a cell with a packaging vector prior to introducing a packageable nucleic acid into the cell line simplifies the logistics of making several separate cell lines, each of which packages, e.g., a separate packageable nucleic acid.

Cell supernatants from the packaging cell lines are also a feature of the invention. The supernatant from a packaging cell line includes HIV particles which comprise an HIV packageable nucleic acid. The concentration of such particles is typically at least about $10^3$ or $10^4$ to about $10^5$ transducing units per ml or more, more preferably at least about $10^4$ to about $10^6$ transducing units per ml or more, and most preferably at least about $10^5$ transducing units per ml or more. In one embodiment, the invention provides a cell supernatant comprising an HIV-based vector produced by a method of manufacturing the supernatant. In the method, a target nucleic acid is incubated in a packaging cell line having a packaging vector nucleic acid which encodes an HIV-1 particle (the packaging vector typically has the Vpr accessory genes of HIV-1). The particle, when expressed, comprises reverse transcriptase activity, is non-infectious, and is competent to package RNA with a titre of at least $10^4$ transducing units per ml, wherein the RNA has an HIV-1 packaging site, the particles do not package the packaging vector nucleic acids as detected by RT-PCR, and, the packaging vector comprises a deletion of more than one stem loop of the Ψ structure. The target nucleic acid is packaged in the cell into an HIV-1 particle, producing a packaged target nucleic acid and the cells are cultured to produce a cell supernatant comprising the packaged target nucleic acid.

In one embodiment, the present invention provides a method of transducing a target cell with an HIV-packageable target nucleic acid. In the method, a packaging cell line made as set forth herein is used to package a packageable target nucleic acid into an HIV particle. The HIV particle is then incubated with the target cell, thereby transducing the target cell (typically a CD4$^+$ cell) with the target packageable nucleic acid. In this method, the target cell is ordinarily CD4$^+$, since the target packageable nucleic acid gains entry to the target cell by interaction between the HIV particle packaging the target nucleic acid and the target cell (CD4 is the cellular receptor which recognizes the HIV particle). However, HIV particles transduce some CD4_ cells in vitro. In addition, HIV particles are pseudotyped to transduce many other cell types, including hematopoietic stem cells (CD34$^+$), which are also preferred cellular targets.

In one preferred embodiment, the transformation of the target cell with the target packageable nucleic acid renders the target cell resistant to HIV infection. This is accomplished by encoding an anti-HIV viral inhibitor in the target packageable nucleic acid, such as an anti-HIV ribozyme, transdominant gene, or suicide gene. Thus, the invention is useful, inter alia, in providing methods of transforming cells, and in rendering cells HIV resistant. HIV resistant cells are useful in vitro to reduce the risk of handling cells, e.g., in tissue culture techniques, and in ex vivo and in in vivo gene therapy procedures.

One aspect of the present invention is the discovery that the HIV-2 packaging site is competent to be packaged by an HIV-1 packaging cell line. In other words, the HIV-1 gag proteins package nucleic acids comprising an HIV-2 packaging site. Thus, the invention provides HIV-2 derived nucleic acids packaged into viral particles containing HIV-1 gag proteins to yield a cell transformation vector. HIV packageable HIV-2 derived nucleic acids include an HIV-2 packaging site, and optionally other HIV-2 elements such as HIV-2 LTRs, polymerase genes, structural genes and the like. The use of HIV-2 derived nucleic acids in HIV-1 particles provides a particularly preferred cell transformation vector, because HIV-2 nucleic acids do not typically recombine with HIV-1 nucleic acids, making the HIV-2 based nucleic acids safer than those which incorporate HIV-1 derived nucleic acids.

A particularly preferred HIV-2 clone to use as a source for HIV-2 nucleic acid elements is the HIV-$2_{KR}$ clone. In particular, the HIV-$2_{KR}$ LTRs are Rev independent, and the HIV-$2_{KR}$ packaging site is packaged by HIV-1 particles, e.g. in an HIV packaging cell. In addition, the clone has low pathogenicity and is infective in HIV model animals such as macaques.

In one particularly preferred embodiment, the HIV-2 derived nucleic acid packaged by the HIV-1 particle has a nuclear export signal. For instance, the MPMV nucleic acid nuclear export subsequence is a preferred nuclear export signal. The use of a nuclear export signal eliminates the need for Rev in transport of HIV-derived nucleic acid from the nucleus to the cytoplasm of a cell where they are translated. In other embodiments, an RRE or partial RRE signal is provided for co-localization of a therapeutic vector and an HIV target nucleic acid.

The cell transformation vectors of the invention typically include transcription cassettes which are expressed by the cell to be transformed. The transcription cassettes preferably include constitutive promoters such as pol III promoters (e.g., those from the t-RNA genes, such as t-RNAval) or pol II promoters (e.g., strong promoters such as those derived from structural genes such as actin, or viral genes such as those found in adenovirus), or utilize the natural promoters found in an HIV LTR. The transcription cassettes comprise genes of interest such as therapeutic nucleic acids (e.g., ribozymes and anti-sense molecules), suicide genes, transdominant genes, cellular enzymes and the like. In addition, HIV vectors are found to have intrinsic anti-HIV activity. The transcription cassettes are cloned between HIV-2 LTRs, or into the LTRs to reduce promoter interference. In one preferred embodiment, multiple transcription cassettes are included in the nucleic acid, some located internal to the LTRs and some between the LTRs of the cell transformation vector.

Accordingly, the invention also provides ways of transforming a cell, e.g, using the cell transformation vectors of the invention. In general, the cell transformation vectors of the invention are contacted to a target cell, permitting transduction of the nucleic acid encoded by the vector into the cell. The nucleic acid is then expressed, or is incorporated into the cellular genome, e.g. by HIV-2 LTRs which are part of the vector. The cells are typically isolated from a cell culture or a mammal. They are optionally reintroduced into a mammal after transduction by a cell transformation vector.

In one embodiment, the cells transformed are hematopoietic stem cells such as $CD34^+$ stem cells. Stem cells transformed by the methods are typically introduced into a mammal. In one particular embodiment, the cell transformation encodes an anti-HIV agent such as a ribozyme which cleaves an HIV nucleic acid. In this embodiment, cells transformed with the vectors and their differentiated progeny are HIV-resistant.

DEFINITIONS

Figure 1:
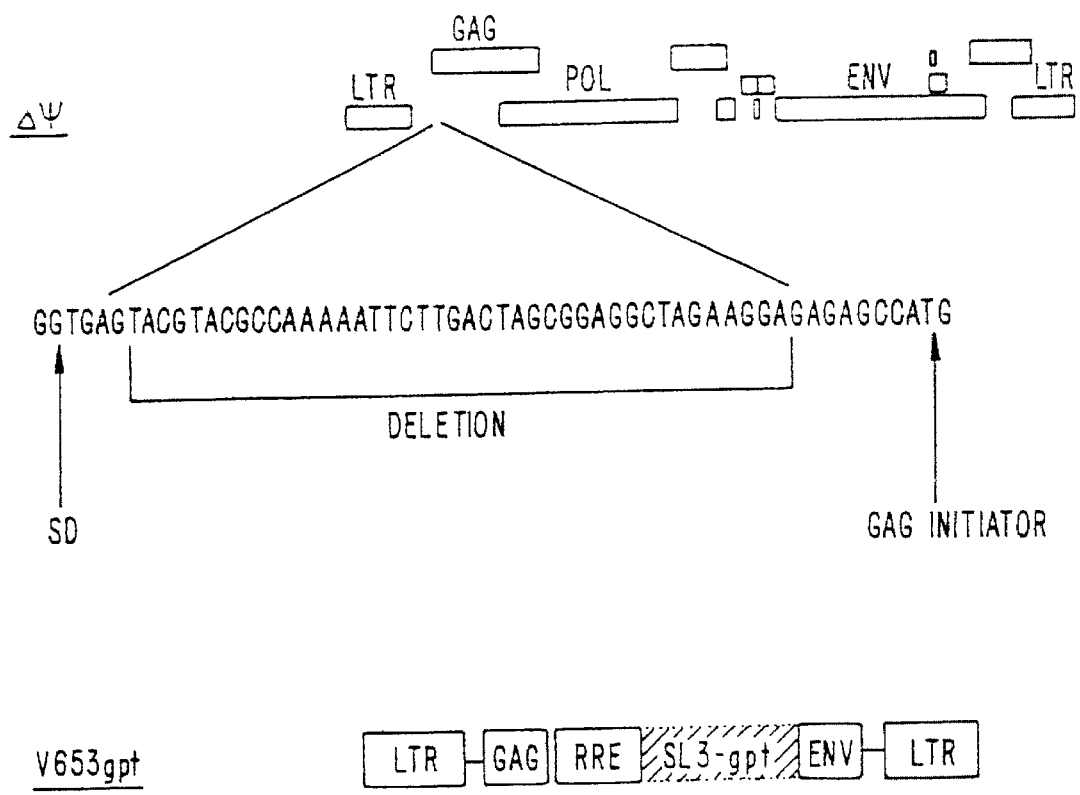
FIG. 1 shows the structures of the $\Delta\psi$ packaging plasmid and the V653gpt vector. The position of the major splice donor site (MSD), and of the Rev Responsive Element (RRE) are indicated. The deleted sequence corrresponds to SEQ ID NO:1.

Unless defined otherwise, all technical and scientific terms used herein have the same meaning as commonly understood by one of ordinary skill in the art to which this invention belongs. Singleton et al. (1994) *Dictionary of Microbiology and Molecular Biology,* second edition, John Wiley and Sons (New York) provides one of skill with a general dictionary of many of the terms used in this invention. Although any methods and materials similar or equivalent to those described herein can be used in the practice or testing of the present invention, the preferred methods and materials are described. For purposes of the present invention, the following terms are defined below.

A "vector" is a composition which can transduce, transform or infect a cell, thereby causing the cell to express nucleic acids and/or proteins other than those native to the cell, or in a manner not native to the cell. A vector includes a nucleic acid (ordinarily RNA or DNA) to be expressed by the cell (a "vector nucleic acid"). A vector optionally includes materials to aid in achieving entry of the nucleic acid into the cell, such as a viral particle, liposome, protein coating or the like. A "cell transformation vector" is a vector which encodes a nucleic acid capable of transforming a cell once the nucleic acid is transduced into the cell.

A "packaging vector" is a vector which encodes components necessary for production of HIV particles by a cell transduced by the packaging vector. The packaging vector optionally includes all of the components necessary for production of HIV particles, or optionally includes a subset of the components necessary for HIV packaging. For instance, in one preferred embodiment, a packaging cell is transformed with more than one packaging vector, each of which has a complementary role in the production of an HIV particle.

Two (or more) HIV-based packaging vectors are "complementary" when they together encode all of the functions necessary for HIV packaging, and when each individually does not encode all of the functions necessary for packaging. Thus, e.g., when two vectors transduce a single cell and together they encode the information for production of HIV packaging particles, the two vectors are "complementary". The use of complementary vectors is preferred because it increases the safety of any packaging cell made by transformation with a packaging vector by reducing the possibility that a recombination event will produce an infective virus.

Packaging vectors encode HIV particles. The HIV particles are competent to package target RNA which has an HIV packaging site. "High efficiency packaging vectors" package target RNAs such that packaging cells stably transformed with the packaging vector and transformed with a target packageable nucleic acid corresponding to the target packageable RNA produce packaged target RNA at a titer of at least about $10^3$ or $10^4$ to about $10^5$ transducing units per ml or more, more preferably at least about $10^4$ to about $10^6$ transducing units per ml or more, and most preferably at least about $10^5$ transducing units per ml or more. The precise titer which is produced varies depending on the nature of the packageable nucleic acid. For example, the minimal plasmid V0gpt is packaged less efficiently than the plasmid V653gpt (see, the examples herein), because it does not have as complete a packaging site. Thus, higher infectivities are typically obtained when packaging plasmids with complete packaging sites. Preferred cell lines package the plasmid V653gpt with a titer of $10^4$ to about $10^5$ transducing units per ml or more, more preferably at least about $10^4$ to about $10^6$ transducing units per ml or more, and most preferably at least about $10^5$ transducing units per ml or more.

An HIV-1-MN clone is a clone derived from the publicly available HIV-1-MN genomic clone (Hall et al. (1992) *J. Virol* 66 (9) 5553–5560) by standard recombinant techniques such as subcloning, site-directed mutagenesis and the like, or, alternatively, an artificial nucleic acid synthesized based upon the HIV-1-MN genomic sequence. An example HIV-1-MN clone is the high efficiency packaging clone $\Delta\Psi$ which is derived from the HIV-1-MN genomic sequence by deletion of the HIV-1 packaging site. Packaging vector nucleic acids of the invention that are based on HIV-1MN have a deletion in the HIV packaging site, rendering the nucleic acid unpackageable by an HIV virus.

An "inhibitor" or "viral inhibitor" is most typically a nucleic acid which encodes an active anti-viral agent, or is itself an anti-viral agent. Thus, in one class of embodiments, the inhibitor is a "direct inhibitor," i.e., the inhibitor acts directly on a viral component to inhibit the infection, replication, integration or growth of the virus in the cell. For instance, in one particularly preferred embodiment, the inhibitor comprises a trans-active ribozyme which cleaves an HIV transcript. In this configuration, the inhibitor is typically an RNA molecule with catalytic nuclease activity. In another class of embodiments, the inhibitor is an "indirect inhibitor," i.e., the inhibitor encodes the direct inhibitor. An inhibitor "encodes" a direct inhibitor such as an active ribozyme, RNA molecular decoy, or anti-sense RNA if it contains either the sense or anti-sense coding or complementary nucleic acid which corresponds to the direct inhibitor. By convention, direct inhibitor RNAs such as ribozymes are typically listed as their corresponding DNA sequences. This is done to simplify visualization of the corresponding active RNA, which is equivalent to the given sequence with the T residues replaced by U residues.

"Viral inhibition" refers to the ability of a component to inhibit the infection, growth, integration, or replication of a virus in a cell. Inhibition is typically measured by monitoring changes in a cell's viral load (i.e., the number of viruses and/or viral proteins or nucleic acids present in the cell, cell culture, or organism) or by monitoring resistance by a cell, cell culture, or organism to infection.

A "promoter" is an array of nucleic acid control sequences which direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

A "constitutive" promoter is a promoter which is active under most environmental and developmental conditions. An "inducible" promoter is a promoter which is under environmental or developmental regulation.

The terms "isolated" or "biologically pure" refer to material which is substantially or essentially free from components which normally accompany it as found in its native state.

The term "heterologous" when used with reference to a nucleic acid indicates that the nucleic acid comprises two or more subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous.

The term "identical" in the context of two nucleic acid or polypeptide sequences refers to the residues in the two sequences which are the same when aligned for maximum correspondence. When percentage of sequence identity is used in reference to proteins or peptides it is recognized that residue positions which are not identical often differ by conservative amino acid substitutions, where amino acids residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4: 11–17 (1988) e.g., as implemented in the program PC/GENE (Intelligenetics, Mountain View, Calif., USA).

A "comparison window", as used herein, refers to a segment of at least about 50 contiguous positions, usually about 50 to about 200, more usually about 100 to about 150 in which a sequence is compared to a reference sequence of the same number of contiguous positions after the two sequences are optimally aligned.

Methods of alignment of sequences for comparison are well known in the art. Optimal alignment of sequences for comparison may be conducted by the local homology algorithm of Smith and Waterman (1981) Adv. Appl. Math. 2: 482; by the homology alignment algorithm of Needleman and Wunsch (1970) J. Mol. Biol. 48: 443; by the search for similarity method of Pearson and Lipman (1988) Proc. Natl. Acad. Sci. USA 85: 2444; by computerized implementations of these algorithms (including, but not limited to CLUSTAL in the PC/Gene program by Intelligenetics, Mountain View, Calif., GAP, BESTFIT, FASTA, and TFASTA in the Wisconsin Genetics Software Package, Genetics Computer Group (GCG), 575 Science Dr., Madison, Wis., USA); the CLUSTAL program is well described by Higgins and Sharp (1988) Gene, 73: 237–244 and Higgins and Sharp (1989) CABIOS 5: 151–153; Corpet, et al. (1988) Nucleic Acids Research 16, 10881–90; Huang, et al. (1992) Computer Applications in the Biosciences 8, 155–65, and Pearson, et al. (1994) Methods in Molecular Biology 24, 307–31. Alignment is also often performed by inspection and manual alignment.

"Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in any described sequence. Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) *Proteins* W. H. Freeman and Company. Finally, the addition of sequences which do not alter the activity of a nucleic acid molecule, such as a non-functional sequence is a conservative modification of the basic nucleic acid.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes* part I chapter 2 "overview of principles of hybridization and the strategy of nucleic acid probe assays", Elsevier, N.Y. Generally, highly stringent hybridization and wash conditions are selected to be about 5° C. lower than the thermal melting point ($T_m$) for the specific sequence at a defined ionic strength and ph. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2× SSC wash at 65° C. for 15 minutes (see, Sambrook, supra for a description of SSC buffer). Often the high stringency wash is preceded by a low stringency wash to remove background probe signal. An example low stringency wash is 2× SSC at 40° C. for 15 minutes. In general, a signal to noise ratio of 2× (or higher) than that observed for an unrelated probe in the particular hybridization assay indicates detection of a specific hybridization.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

An "HIV-1 gag protein" is a protein encoded by the HIV-1 gag gene. The gag proteins are typically translated as a large preprotein which is cleaved to form the structural core proteins (e.g., p17 and p24) which package wild-type HIV genomic RNA. A truncated gag protein is a protein produced from a gag protein with a deletion relative to the wild-type sequence.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "recombinant" when used with reference to a cell indicates that the cell replicates or expresses a nucleic acid, or expresses a peptide or protein encoded by nucleic acid whose origin is exogenous to the cell. Recombinant cells can express genes that are not found within the native (non-recombinant) form of the cell. Recombinant cells can also express genes found in the native form of the cell wherein the genes are re-introduced into the cell by artificial means.

A "recombinant expression cassette" or simply an "expression cassette" is a nucleic acid construct, generated recombinantly or synthetically, with nucleic acid elements which permit transcription of a particular nucleic acid in a cell. The recombinant expression cassette can be part of a plasmid, virus, or nucleic acid fragment. Typically, the recombinant expression cassette includes a nucleic acid to be transcribed, and a promoter. In some embodiments, the expression cassette also includes, e.g., an origin of replication, and/or chromosome integration elements (e.g., a retroviral LTR).

The term "subsequence" in the context of a particular nucleic acid sequence refers to a region of the nucleic acid equal to or smaller than the specified nucleic acid.

A virus or vector "transduces" a cell when it transfers nucleic acid into the cell. A cell is "transformed" by a nucleic acid when a nucleic acid transduced into the cell becomes stably replicated by the cell, either by incorporation of the nucleic acid into the cellular genome, or by episomal replication. A virus or vector is "infective" when it transduces a cell, replicates, and (without the benefit of any complementary virus or vector) spreads progeny vectors or viruses of the same type as the original transducing virus or vector to other cells in an organism or cell culture, wherein the progeny vectors or viruses have the same ability to reproduce and spread throughout the organism or cell culture. Thus, for example, a nucleic acid encoding an HIV particles is not infective if the nucleic acid cannot be packaged by the HIV particle (e.g., if the nucleic acid lacks an HIV packaging site), even though the nucleic acid can be used to transfect and transform a cell. Similarly, an HIV-packageable nucleic acid packaged by an HIV particle is not infective if it does not encode the HIV particle that it is packaged in, even though it may be used to transform and transfect a cell. If an HIV-packageable nucleic acid is used to transform a cell infected with HIV in a cell culture or organism infected with HIV, the HIV-packageable nucleic acid will be replicated and disseminated throughout the organism in concert with the infecting HIV virus. However, the HIV-packageable nucleic acid is not itself "infective", because packaging functions are supplied by the infective HIV virus via trans complementation.

A cell "supernatant" is the culture medium in which a cell is grown. The culture medium includes material from the cell, including, e.g., HIV viral particles which bud off from the cell membrane and enter the culture medium.

Detailed Discussion of the Invention

This invention provides HIV packaging cell lines, nucleic acids packaged by those cell lines and vectors comprising the packaged nucleic acids. In particular, this invention overcomes prior art deficiencies by providing well characterized HIV packaging cells with titers of $10^4$ to $10^6$ TU/ml. Furthermore, it is now discovered that such packaging cells are competent to package both HIV-1 and HIV-2 derived nucleic acids, i.e., nucleic acids with either an HIV-1 or HIV-2 packaging site. Accordingly, one aspect of the invention provides an HIV-2 nucleic acid packaged in an HIV-1 based particle.

The packaging systems provided herein differ from prior art packaging systems in several respects. First, the packaging virions described so far have been derived from the HXBc2 plasmid. HXBc2 packaging virions are abnormal, with unprocessed p55$^{Gag}$ protein (Carroll, et al. (1994) *J. Virol.* 68(9):6047–6051), disproportionately low reverse transcriptase (RT) activity (Carroll, et al. (1994) *J. Virol.* 68(9):6047–6051; Lever, et al. (1989) *J. Virol.* 63(9):4085–4087), and/or immature morphology revealed by electron microscopy (Aldovini, et al. (1990) *J. Virol.* 64(5):1920–1926; Clavel, et al. (1990) *J. Virol.* 64(10):5230–5234). It is now discovered that some of these deficiencies stem from the fact that HXBc2 lacks a full complement of the viral accessory genes, e.g. the vpr gene is truncated (Ratner, et al. (1987) *AIDS Res. Hum. Retroviruses* 3:57–69). Secondly, the packaging vectors used herein typically contain all of the RNA sequences that are involved in optimal HIV-1 packaging, whereas others have used vectors devoid of gag and/or env sequences. Third, in preferred embodiments, adherent Hela-T4 cells are used to titer g cell supernatants, rather than CD4$^+$ lymphoid T cells. The selection of untransduced cells is more efficient using adherent cells than using nonadherent cells, since the untransduced, dead cells are removed by washing, and toxicity is minimized. Fourth, the packaging cells are preferably stably transduced with a packaging vector before the packaging cells are transduced with a packageable nucleic acid, which reduces the likelihood for a recombination event leading to an infective virus. Fifth, the packaging cell lines of the invention include a packaging vector nucleic acid which encodes a functional vpr gene.

The establishment of stable cell lines producing high titers of fully characterized transducing particles is a major step forward in the utilization of HIV-derived constructs for gene therapy. One new class of vectors described herein comprise HIV-2 derived nucleic acids packaged in HIV-1 capsids. In addition to applications for therapy against HIV infection, the ability of HIV vectors to target CD4$^+$ lymphocytes as well as non-dividing cells such as cells of the monocyte/macrophages lineages, renders this vector/packaging system useful for targeting other hematopoietic disorders which are affected by CD4$^+$ cells. These include a number of T-cell lymphomas, HTLV-1 infection, Adult T cell leukemia, Myosis Fungsides and Segary's syndromes, CD4$^+$ lymphoblastic lymphomas, and peripheral CD4$^+$ T cell lymphomas. In addition, the invention, by providing a methods and compositions for transducing CD4$^+$ and CD34$^+$ cells in general, provides methods and compositions useful in general for the transformation of cells, both in vitro and in vivo. Thus, the invention is useful as a general laboratory technique for the transformation of cells in cloning procedures.

Making Packaging Vectors and Packageable Nucleic Acids

The present invention provides a variety of packaging vectors and packageable nucleic acids as described supra. Packaging vectors include HIV-derived nucleic acids, particularly those derived from HIV-1-MN. Packageable nucleic acids encode RNAs which comprise an HIV packaging site (HIV-1 or HIV-2 derived), and optionally comprise other HIV-based nucleic acids, or heterologous nucleic acids. In particularly preferred embodiments, the packageable nucleic acids comprise HIV-2 components, including HIV-2 LTRs and packaging sites. One aspect of the invention is the discovery that the HIV-2 packaging site is packaged by the HIV-1 packaging machinery into HIV-1 particles.

The packaging vectors of the invention are derived from HIV-1 clones. Many such clones are known to persons of skill, and publicly available. Well-established repositories of sequence information include GenBank, EMBL, DDBJ and the NCBI. Well characterized HIV clones include HIV-1-MN and HIV-1-MN-ST.1 (Hall et al. (1992) *J. Virol* 66 (9) 5553–5560).

Furthermore, viral clones can be isolated from wild-type HIV viruses using known techniques. Typically, a lambda-phage clone, containing a full-length HIV provirus, is obtained from the genomic DNA of a lymphoblastic cell line infected with an HIV strain isolated from the peripheral blood mononuclear cells of an HIV seropositive AIDS patient. The virus is replication competent in vitro, producing p24 protein and infectious progeny virions after direct transfection into CD4$^+$ cells. Appropriate cells for testing infectivity include well characterized established human T-cells such as Molt-4/8 cells, SupT1 cells, H9 cells, C8166 cells and myelomonocytic (U937) cells as well as primary human lymphocytes, and primary human monocyte-macrophage cultures. In general, a complete virulent HIV viral genome can be used to make a packaging vector. A "full-length HIV genome" in relation to an HIV-1 packaging vector consists of a nucleic acid (RNA or DNA) encoded by an HIV virus or viral clone which includes the 5' and 3' LTR regions and the genes between the LTR regions which are present in a typical wild-type HIV-1 virus (e.g., env, nef, rev, vpx, tat, gag, pol, vif, and vpr).

The packaging vector is made by deleting the HIV packaging site from a full-length HIV genome. Specific mutations in the HIV packaging site are described, e.g., in Aldovini and Young (1990) *Journal of Virology* 64(5): 1920–1926. The RNA secondary structure of the packaging site is described in Clever et al. (1995) *Journal of Virology* 69(4): 2101–2109. The stem loops of the psi site for HIV-1 are described in Clever. In the packaging vectors of the invention, at least two of the four stem loops are deleted or substantially mutated to prevent loop formation. Preferably, three loops are deleted or mutated, and more preferably all four loops are deleted or mutated.

In the packaging vectors of the invention, nucleic acids corresponding to at least two, and preferably three or all of the four stem loops of the Ψ structure are typically deleted from a clone of an HIV-1 viral genome. This results in substantial deletion in the region between the major splice donor site ("MSD") and the beginning of the gag gene. For instance, the ΔΨ plasmid described herein has a 37 base-pair deletion between the MSD and the beginning of the gag gene. Prior art deletion clone packaging vectors typically did not delete as large a portion of the packaging site, which resulted in partially infective packaging vectors (i.e., attenuated, but still infective forms of HIV, which are unsuitable for use in packaging cells, and in producing high titers of packaged HIV-packageable nucleic acids, due to the risk of infection by the attenuated virus).

The resulting deletion clones of the invention can be used to make viral particles, by transducing the deletion clone into a packaging cell (typically a Hela or other well-characterized cell) and expressing the clone. Because the clones lack the HIV packaging site, they are not packaged into the viral particles.

To increase the safety of the transduced packaging cells, it is preferable to cut (e.g., by subcloning) the deletion clone (or homologous clones) into multiple expression clones with complementary functions. This decreases the chances that a recombination event will result in an infectious particle.

Packageable nucleic acids encode an RNA which is competent to be packaged by an HIV particle. Such nucleic acids can be constructed by recombinantly combining an HIV packaging site with a nucleic acid of choice. The packaging site (psi site) is located adjacent to the 5' LTR, primarily between the MSD site and the gag initiator codon (AUG) in the leader sequence of the gag gene. Thus, the minimal HIV-1 packaging site includes a majority of nucleic acids between the MSD and the gag initiator codon from either HIV-1 or HIV-2. See also, Clever et al., supra and Garzino-Demo et al. (1995) *Hum. Gene Ther.* 6(2): 177–184. For a general description of the structural elements of the HIV genome, see, Holmes et al. PCT/EP92/02787. Preferably, a complete packaging site includes sequences from the 5' LTR and the 5' region of gag gene for maximal packaging efficiency. These packaging sequences typically include a portion of the gag gene, e.g., extending about 100 bases into the coding region of gag or further, and about 100 bases into the HIV 5' LTR or further. More preferably, the first 100–700 nucleotides from the gag gene are included. Yet more preferably, the first 500–660 nucleotides of gag are included. Most preferably, about the first 650 nucleotides of gag are included. In one well characterized embodiment (see, example 2) the first 653 nucleotides of gag are included. Alternatively, the vector V0gpt, described supra, includes a minimal HIV packaging site in conjunction with HIV LTRs, and is shown to be packageable by the cells of the invention. In addition, sequences from the env gene are preferably included in the packaging site, particularly the RRE. An example preferred packaging site is the packaging site from V653gpt described herein.

When an HIV-2 packaging site is used, the first ATG of gag to the MSD is preferably included as the HIV-2 packaging site. Still more preferably, the first 30 nucleotides of gag are also included as part of the HIV-2 packaging site. Typically, the first 50 nucleotides of gag are also included as part of the HIV-2 packaging site. Often the first 75 nucleotides of gag are also included as part of the HIV-2 packaging site. Generally, the first 100 nucleotides of gag are also included as part of the HIV-2 packaging site.

Given the strategy for making the packaging and target packageable nucleic acids of the present invention, one of skill can construct a variety of clones containing functionally equivalent nucleic acids. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, N.Y., (Sambrook); and *Current Protocols in Molecular Biology,* F. M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

The nucleic acid compositions of this invention, whether RNA, cDNA, genomic DNA, or a hybrid of the various combinations, are isolated from biological sources or synthesized in vitro. The nucleic acids of the invention are present in transformed or transfected whole cells, in transformed or transfected cell lysates, or in a partially purified or substantially pure form.

In vitro amplification techniques suitable for amplifying sequences for use as molecular probes or generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039.

Oligonucleotides for use as probes, e.g., in in vitro amplification methods, for use as gene probes, or as inhibitor components (e.g., ribozymes) are typically synthesized chemically according to the solid phase phosphoramidite triester method described by Beaucage and Caruthers (1981), *Tetrahedron Letts.,* 22(20):1859–1862, e.g., using an automated synthesizer, as described in Needliam-VanDevanter et al. (1984) *Nucleic Acids Res.,* 12:6159–6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560.

Making Conservative Substitutions

One of skill will appreciate that many conservative variations of the nucleic acid constructs disclosed yield a functionally identical construct. For example, due to the degeneracy of the genetic code, "silent substitutions" (i.e., substitutions of a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence of a packaging or packageable construct are substituted with different amino acids with highly similar properties (see, the definitions section, supra), are also readily identified as being highly similar to a disclosed construct. Such conservatively substituted variations of each explicitly disclosed sequence are a feature of the present invention.

One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) *Gene* 8:81–97, Roberts et al. (1987) *Nature* 328:731–734 and Sambrook, Innis, Ausbel, Berger, Needham VanDevanter and Mullis (all supra).

One of skill can select a desired nucleic acid of the invention based upon the sequences provided and upon knowledge in the art regarding HIV generally. The life-cycle, genomic organization, developmental regulation and associated molecular biology of HIV viruses have been the focus of over a decade of intense research. The specific effects of many mutations in the HIV genome are known. Moreover, general knowledge regarding the nature of proteins and nucleic acids allows one of skill to select appropriate sequences with activity similar or equivalent to the nucleic acids and polypeptides disclosed in the sequence listings herein. The definitions section herein describes exemplar conservative amino acid substitutions.

Finally, most modifications to nucleic acids are evaluated by routine screening techniques in suitable assays for the desired characteristic. For instance, changes in the immunological character of encoded polypeptides can be detected by an appropriate immunological assay. Modifications of other properties such as nucleic acid hybridization to a complementary nucleic acid, redox or thermal stability of encoded proteins, hydrophobicity, susceptibility to proteolysis, or the tendency to aggregate are all assayed according to standard techniques.

Making Stable Packaging Cell Lines

Stable packaging cell lines are made by stably transforming a mammalian cell with a packaging vector. The transformation of mammalian cells is known in the art. Host cells are competent or rendered competent for transformation by various known means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, receptor-mediated endocytosis, electroporation and micro-injection of the DNA directly into the cells.

The culture of cells used in conjunction with the present invention, including cell lines and cultured cells from tissue or blood samples is well known in the art. Freshney (*Culture of Animal Cells, a Manual of Basic Technique, third edition* Wiley-Liss, New York (1994)) and the references cited therein provides a general guide to the culture of cells. Transformed cells are cultured by means well known in the art. See, also Kuchler et al. (1977) *Biochemical Methods in Cell Culture and Virology,* Kuchler, R. J., Dowden, Hutchinson and Ross, Inc. Mammalian cell systems often will be in the form of monolayers of cells, although mammalian cell suspensions are also used. Illustrative examples of mammalian cell lines include VERO and Hela cells, Chinese hamster ovary (CHO) cell lines, W138, BHK, Cos-7 or MDCK cell lines (see, e.g., Freshney, supra).

Supernatants from cell cultures of the packaging cells of the invention are obtained using standard techniques such as those taught in Freshney, supra. See also, Corbeau et al. (1996) *Proc. Natl. Acad. Sci. USA* 93:14070–14075 and the references therein. Components from the cell supernatants can be further purified using standard techniques. For example, HIV particles in the supernatant can be purified from the supernatant by methods typically used for viral purification such as centrifugation, chromatography, affinity purification procedures, and the like.

Transforming mammalian cells with nucleic acids can involve, for example, incubating competent cells with a plasmid containing nucleic acids which code for an HIV particle. The plasmid which is used to transform the host cell preferably contains nucleic acid sequences to initiate transcription and sequences to control the translation of the encoded sequences. These sequences are referred to generally as expression control sequences. Illustrative mammalian expression control sequences are obtained from the SV-40 promoter (*Science* (1983) 222:524–527), the CMV I.E. Promoter (*Proc. Natl. Acad. Sci.* (1984) 81:659–663) or the metallothionein promoter (*Nature* (1982) 296:39–42). A cloning vector containing expression control sequences is cleaved using restriction enzymes and adjusted in size as necessary or desirable and ligated with DNA coding for the HIV sequences of interest by means well known in the art.

Polyadenlyation or transcription terminator sequences from known mammalian genes are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague et al. (1983) *J. Virol.* 45: 773–781). Additionally, gene sequences to control replication in a particular host cell are incorporated into the vector such as those found in bovine papilloma virus type-vectors. See, Saveria-Campo (1985), "Bovine Papilloma virus DNA a Eukaryotic Cloning Vector" in *DNA Cloning Vol. II a Practical Approach* Glover (ed) IRL Press, Arlington, Va. pp. 213–238.

Co-plasmids can be used in selection methods. In these methods, a plasmid containing a selectable marker, such as an antibiotic resistance gene, is used to co-transfect a cell in conjunction with a plasmid encoding HIV packaging nucleic acids. The cells are selected for antibiotic resistance, and the presence of the plasmid of interest is confirmed by Southern analysis, northern analysis, or PCR. Co-plasmids encoding proteins to be expressed on the surface of an HIV particle (e.g., proteins which expand the host range of the capsid such as the VSV envelope, a cell receptor ligand, or an antibody to a cell receptor) are optionally transduced into the packaging cell. In addition to VSV, the envelope proteins of other lipid enveloped viruses are optionally incorporated into a particle of the invention, thereby expanding the transduction range of the particle.

Viral vectors (e.g., retroviral or adeno-associated viral vectors) containing nucleic acids which encode HIV sequences are also used to transform cells within the host range of the vector. See, e.g., *Methods in Enzymology,* vol. 185, Academic Press, Inc., San Diego, Calif. (D. V. Goeddel, ed.) (1990) or M. Krieger, *Gene Transfer and Expression—A Laboratory Manual,* Stockton Press, New York, N.Y., (1990) and the references cited therein.

Once stable transformed cell lines are made which express HIV particles, the transformed cell lines are transfected with vectors which encode nucleic acids to be incorporated into the HIV vectors. Typically, these vectors are plasmids or are coded in viral vectors. The packaged nucleic acids include an HIV packaging site subsequence in conjunction with a sequence of interest, such as a viral inhibitor or other gene therapeutic.

Hela cells are preferred packaging cell lines, and can be made competent for transformation by the techniques described above. For example, to generate a stable HIV-1 packaging cell line, Hela cells were transfected by the Calcium-Phosphate method. A subconfluent Hela culture in a 6-well plate (Costar, Cambridge, Mass.) was transfected with linearized and Calcium-Phosphate precipitated plasmid $\Delta\psi$ (10 $\mu$g) and plasmid SV-NEO containing the neo$^r$ gene driven by the SV40 promotor (0.6 $\mu$g) in Dulbecco's modified Eagle's medium supplemented with 10% FCS, antibiotics and glutamine (DMEM-10% FCS). After 18 hours, wells were washed with Dulbecco's phosphate-buffered saline (PBS) pH 7.8, incubated for 2 min. at 20° C. with 15% glycerol solution in HEPES-buffered saline (50 mM HEPES pH 7.1, 280 mM NaCl, 1.5 mM Na2HP04), washed twice with PBS and cultured in DMEM-10% FCS. At day 3, 500 $\mu$g/ml G418 (Gibco BRL, Grand Island, N.Y.) was added to the cell culture. $\psi$422 cells were transfected with 10 $\mu$g of V653gpt by the same method.

Assaying for HIV Packaging Vectors, Packageable Nucleic Acids and HIV Particles in Packaging Cell Lines, Target Cells and Cell Lysates A wide variety of formats and labels are available and appropriate for detection of packaging vectors, packageable nucleic acids and HIV particles in packaging cells, target cells, patients and cell lysates. HIV antibodies, and the polypeptides and nucleic acids of the invention are detected and quantified by any of a number of means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like. Several commercially available ELISA assays for the detection of HIV components are available, allowing one of skill to detect HIV particles, or HIV virus in a biological sample.

The detection of nucleic acids proceeds by well known methods such as Southern analysis, northern analysis, gel electrophoresis, PCR, radiolabeling and scintillation counting, and affinity chromatography. Many assay formats are appropriate, including those reviewed in Tijssen (1993) *Laboratory Techniques in biochemistry and molecular biology—hybridization with nucleic acid probes* parts I and II, Elsevier, New York and Choo (ed) (1994) *Methods In Molecular Biology Volume 33—In Situ Hybridization Protocols* Humana Press Inc., New Jersey (see also, other books in the Methods in Molecular Biology series); see especially, Chapter 21 of Choo (id) "Detection of Virus Nucleic Acids by Radioactive and Nonisotopic in Situ Hybridization". A variety of automated solid-phase detection techniques are also appropriate. For instance, very large scale immobilized polymer arrays (VLSIPS™) are used for the detection of nucleic acids. See, Tijssen (supra), Fodor et al. (1991) *Science,* 251: 767–777 and Sheldon et al. (1993) *Clinical Chemistry* 39(4): 718–719. Finally, PCR is also routinely used to detect nucleic acids in biological samples (see, Innis, supra for a general description of PCR techniques).

In one preferred embodiment, antibodies are used to detect proteins expressed by the packaged vector, the packaging nucleic acid or to monitor circulating HIV levels in human blood, e.g., to monitor the in vivo effect of a gene therapeutic agent coded by the packaged nucleic acids. In other embodiments, antibodies are co-expressed in the packaging cells to be incorporated into viral particals. Methods of producing polyclonal and monoclonal antibodies are known to those of skill in the art, and many anti-HIV antibodies are available. See, e.g., Coligan (1991) *Current Protocols in Immunology* Wiley/Greene, NY; and Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) Nature 256: 495–497. Other suitable techniques for antibody preparation include selection of libraries of recombinant antibodies in phage or similar vectors. See, Huse et al. (1989) *Science* 246: 1275–1281; and Ward, et al. (1989) *Nature* 341: 544–546. Specific monoclonal and polyclonal antibodies and antisera will usually bind with a $K_D$ of at least about 0.1 mM, more usually at least about 1 $\mu$M, preferably at least about 0.1 $\mu$M or better, and most typically and preferably, 0.01 $\mu$M or better.

Polypeptides encoded by the nucleic acids of the invention can be used to make antibodies for the detection of HIV particles using known techniques. Polypeptides of relatively short size can be synthesized in solution or on a solid support. See, e.g., Merrifield (1963) *J. Am. Chem. Soc.* 85:2149–2154. Various automatic synthesizers are commercially available and can be used in accordance with known protocols. See, e.g., Stewart and Young (1984) *Solid Phase Peptide Synthesis,* 2d. ed., Pierce Chemical Co. Larger polypeptides can be synthesized recombinantly in prokaryotes or in eukaryotes. See, See, e.g., Sambrook and Ausbel and Berger (all supra) for details concerning cloning and expressing polypeptides, e.g., in *E. coli.* Expression systems for expressing polypeptides are available using *E. coli,* Bacillus sp. (Palva, I. et al., 1983, *Gene* 22:229–235; Mosbach, K. et al., *Nature,* 302:543–545) and Salmonella. *E. coli* systems are the most common, and best defined prokaryotic expression systems and are, therefore, preferred. Expression in yeast and other eukaryotic cells, including mammalian cells is also well known and appropriate. See, e.g., Sherman et al. (1982) *Methods in Yeast Genetics,* Cold Spring Harbor Laboratory. See, e.g., *Methods in Enzymology,* vol. 185, Academic Press, Inc., San Diego, Calif. (D. V. Goeddel, ed.) (1990); M. Krieger, *Gene Transfer and Expression—A Laboratory Manual,* Stockton Press, New York, N.Y., (1990) and the references cited therein; and, Scopes (1982) *Protein Purification: Principles and Practice* Springer-Verlag New York.

Frequently, polypeptides and their corresponding antibodies will be labeled by joining, either covalently or non covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350;

3,996,345; 4,277,437; 4,275,149; and 4,366,241. Also, recombinant immunoglobulins may be produced. See, Cabilly, U.S. Pat. No. 4,816,567; and Queen et al. (1989) *Proc. Nat'l Acad. Sci. USA* 86: 10029–10033.

The culture of cells used in conjunction with the present invention, including cell lines and cultured cells from tissue or blood samples is well known in the art. Freshney (*Culture of Animal Cells, a Manual of Basic Technique, third edition* Wiley-Liss, New York (1994)) and the references cited therein provides a general guide to the culture of cells.

Use of the Nucleic Acids of the Invention as Molecular Probes

In addition to their utility in making HIV packaging cell lines, the non-infective packaging vectors of the invention can be used to detect wild-type HIV in biological samples using Southern or northern blot assays. In brief, the packaging vector is labeled, typically using a radio or bioluminescent label, and used to probe a northern or Southern blot of a sample suspected of containing HV virus. The use of the packaging vector as a probe is safer than the use of an infective virus as a probe. The packaging vector is also more likely to detect a wild type virus than a smaller probe, because, unlike a small probe, the packaging vector probe has virtually the entire genome in common with a wild-type virus, making it improbable that the wild type virus could escape detection by mutation of the probe binding site.

Furthermore, the packaging vectors can be used as positive controls in essentially all known detection methods for the detection of HIV. In this embodiment, a packaging vector nucleic acid or encoded polypeptide is used as a positive control to establish that an HIV detection assay is functioning properly. For instance, oligonucleotides are used as primers in PCR reactions to detect HIV nucleic acids in biological samples such as human blood in clinical settings. The packaging vector, which comprises nucleic acid subsequences corresponding to the region to be amplified is used as an amplification templates in a separate reaction from a test sample such as human blood to determine that the PCR reagents and hybridization conditions are appropriate. Similarly, the polypeptides encoded by the packaging vector can be used to check ELISA reagents in assays for the detection of HIV expression products in biological samples.

Packageable nucleic acids can be used in the same fashion as molecular probes, e.g., when they encode HIV components such as HIV packaging sites, HIV LTRs and the like.

Cellular Transformation and Gene Therapy

The present invention provides packageable nucleic acids for the transformation of cells in vitro and in vivo. These packageable nucleic acids are packaged in HIV-1 particles in the HIV packaging cell lines described herein. The nucleic acids are transfected into cells through the interaction of the HIV particle surrounding the nucleic acid and the HIV cellular receptor. As shown in the examples herein, HIV vectors have anti-HIV activity per se, even without the addition of specific anti-HIV genes such as anti-HIV ribozymes.

Cells which are transfected by HIV particles include $CD4^+$ cells, including T-cells such as Molt-4/8 cells, SupT1 cells, H9 cells, C8166 cells and myelomonocytic (U937) cells as well as primary human lymphocytes, and primary human monocyte-inacrophage cultures, peripheral blood dendritic cells, follicular dendritic cells, epidermal Langerhans cells, megakaryocytes, microglia, astrocytes, oligodendroglia, $CD8^+$ cells, retinal cells, renal epithelial cells, cervical cells, rectal mucosa, trophoblastic cells, and cardiac myocytes (see also, Rosenburg and Fauci 1, supra). Thus, the packageable nucleic acids of the invention are generally useful as cellular transformation vectors.

In one particularly preferred class of embodiments, the packageable nucleic acids of the invention are used in cell transformation procedures for gene therapy. Gene therapy provides methods for combating chronic infectious diseases such as HIV, as well as non-infectious diseases such as cancer and birth defects such as enzyme deficiencies. Yu et al. (1994) *Gene Therapy* 1:13–26 and the references therein provides a general guide to gene therapy strategies for HIV infection. See also, Sodoski et al. PCT/US91/04335. One general limitation of common gene therapy vectors such as murine retroviruses is that they only infect actively dividing cells, and they are generally non-specific. The present invention provides several features that allow one of skill to generate powerful retroviral gene therapy vectors which specifically target $CD4^+$ cells in vivo, and which transform many cell types in vitro. $CD4^+$ cells, including non-dividing cells, are transduced by nucleic acids packaged in HIV particles. HIV particles also infect other cell-types in vitro which exhibit little or no CD4 expression, such as peripheral blood dendritic cells, follicular dendritic cells, epidermal Langerhans cells, megakaryocytes, microglia, astrocytes, oligodendroglia, $CD8^+$ cells, retinal cells, renal epithelial cells, cervical cells, rectal mucosa, trophoblastic cells, and cardiac myocytes (see, Rosenburg and Fauci 1, supra). Thus, these cells can be targeted by the HIV particle-packaged nucleic acids of the invention in ex vivo gene therapy procedures (the infection of these cell types by HIV in vivo, however, is rare), or in drug discovery assays which require transformation of these cell types. Lists of $CD4^+$ and $CD4^-$ cell types which are infectible by HIV have been compiled (see, Rosenburg and Fauci 1 supra; Rosenburg and Fauci (1989) *Adv Immunol* 47:377–431; and Connor and Ho (1992) in *AIDS: etiology, diagnosis, treatment, and prevention,* third edition Hellman and Rosenburg (eds) Lippincott, Philadelphia). In addition, the vectors are optionally pseudotyped for transformation of stem cells.

Pseudotyping the Packageable Vector

Hematopoietic stem cells are particularly preferred targets for cell transformation in general, and for gene therapy (particularly anti-HIV gene therapy) in particular. Packageable vectors are made competent to transform $CD34^+$ cells by pseudotyping the vector. This is done by transducing the packaging cell line used to package the vector with a nucleic acid which encodes the vesicular stomatitis virus (VSV) envelope protein, which is expressed on the surface of the vector. VSV infects both dividing and non-dividing $CD34^+$ cells, and pseudotype vectors expressing VSV envelope proteins are competent to transduce these cells.

Similarly, viral or cellular proteins in general can be co-expressed to increase the host range of an HIV-based vector. Typically, a nucleic acid encoding a selected protein is coexpressed in an HIV packaging cell of the invention. Protein encoded by the nucleic acid is incorporated into the particle which packages an HIV-packageable nucleic acid, which buds off from the packaging cell membrane. If the protein is recognized by a cellular receptor on a target cell, the particle is transduced into the cell by receptor mediated endocytosis. Preferred proteins include viral (particularly retroviral) envelope or coat proteins, cell receptor ligands, antibodies or antibody fragments which bind cell receptors on target cells, and the like.

Preferred Promoters

A preferred class of embodiments utilizes an HIV LTR sequence as a promoter for the HIV packageable vector. These LTR sequences are trans-activated upon infection of a cell containing the LTR promoter by the infecting virus. LTR promoters, in addition to binding tat and rev are responsive to cellular cytokines (such as IL-2 and SP-1) which act to permit transcription of the HIV genome upon infection. Thus, in one embodiment, a therapeutic nucleic acid of choice is placed under the control of an LTR promoter, rendering the cells ordinarily most vulnerable to HIV infection resistant to infection. See, e.g., Poznansky et al. (1991) *Journal or Virology* 65(1): 532–536 for a description of the region flanking the 5' LTR's ability to package vector nucleic acids.

Constitutive promoters for directing expression of therapeutic nucleic acids are also preferred, particularly pol III promoters. Copending applications Ser. No. 08/245,742 (Wong-Staal et al., see also PCT application PCT/US94/05700 (WO 94/26877) and Chatterjee et al. (*Science* (1992), 258: 1485–1488, hereinafter Chatterjee et al. 1) describe anti-sense inhibition of HIV-1 infectivity in target cells using viral vectors with a constitutive pol III expression cassette expressing anti-TAR RNA. Chatterjee et al. (PCT application PCT/US91/03440 (1991), hereinafter Chatterjee et al. 2) describe viral vectors, including AAV-based vectors which express antisense TAR sequences. Chatterjee and Wong (*Methods, A companion to Methods in Enzymology* (1993), 5: 51–59) further describe viral vectors for the delivery of antisense RNA. Copending application Ser. No. 08/442,061, filed May 16, 1995 and the corresponding PCT publication WO 94/26877 (PCT/US94/05700) describes a variety of anti-HIV therapy genes, and gene therapy strategies generally, including the use of suicide genes, trans-dominant genes, ribozymes, anti-sense genes, and decoy genes in gene therapy vectors. Yu et al. (1994) *Gene Therapy* 1: 13–26 and the references cited therein provides a general guide to gene therapy strategies useful against HIV infection. Constitutive HIV-LTR promoters are also known and preferred, such as the HIV-$2_{KR}$ LTR described in copending application Ser. No. 60/001,441.

Ex vivo Transformation of Cells

Ex vivo methods for inhibiting viral replication in a cell in an organism involve transducing the cell ex vivo with a therapeutic nucleic acid of this invention, and introducing the cell into the organism. The cells are typically $CD4^+$ cells such as $CD4^+$ T cells or macrophage isolated or cultured from a patient, or are stein cells. See, e.g., Freshney et al., supra and the references cited therein for a discussion of how to isolate and culture cells from patients. Alternatively, the cells can be those stored in a cell bank (e.g., a blood bank). In one class of preferred embodiments, the packageable nucleic acid encodes an anti-viral therapeutic agent (e.g., suicide gene, trans-dominant gene, anti-HIV ribozymes, anti-sense gene, or decoy gene) which inhibits the growth or replication of an HIV virus, under the control of an activated or constitutive promoter. The cell transformation vector inhibits viral replication in any of those cells already infected with HIV virus, in addition to conferring a protective effect to cells which are not infected by HIV. In addition, in preferred embodiments, the vector is replicated and packaged into HIV capsids using the HIV replication machinery, thereby causing the anti-HIV therapeutic gene to propagate in conjunction with the replication of an HIV virus. Thus, an organism infected with HIV can be treated for the infection by transducing a population of its cells with a vector of the invention and introducing the transduced cells back into the organism as described herein. Thus, the present invention provides a method of protecting cells in vitro, ex vivo or in vivo, even when the cells are already infected with the virus against which protection is sought.

In one particularly preferred embodiment, stein cells (which are typically not $CD4^+$) are used in ex-vivo procedures for cell transformation and gene therapy. The advantage to using stein cells is that they can be differentiated into other cell types in vitro, or can be introduced into a mammal (such as the donor of the cells) where they will engraft in the bone marrow. Methods for differentiating $CD34^+$ cells in vitro into clinically important immune cell types using cytokines such a GM-CSF, IFN-γ and TNF-α are known (see, Inaba et al. (1992) *J. Exp. Med.* 176, 1693–1702, and Szabolcs et al. (1995) 154: 5851–5861). Methods of pseudotyping HIV-based vectors so that they can transform stein cells are described above.

Stem cells are isolated for transduction and differentiation using known methods. For example, in mice, bone marrow cells are isolated by sacrificing the mouse and cutting the leg bones with a pair of scissors. Stem cells are isolated from bone marrow cells by panning the bone marrow cells with antibodies which bind unwanted cells, such as $CD4^+$ and $CD8^+$ (T cells), $CD45^+$ (panB cells), GR-1 (granulocytes), and $Ia^d$ (differentiated antigen presenting cells). For an example of this protocol see, Inaba et al. (1992) *J. Exp. Med.* 176, 1693–1702.

In humans, bone marrow aspirations from iliac crests are performed e.g., under general anesthesia in the operating room. The bone marrow aspirations is approximately 1,000 ml in quantity and is collected from the posterior iliac bones and crests. If the total number of cells collected is $<2\times10^8/$kg, a second aspiration using the sternum and anterior iliac crests in addition to posterior crests is performed. During the operation, two units of irradiated packed red cells are administered to replace the volume of marrow taken by the aspiration. Human hematopoietic progenitor and stem cells are characterized by the presence of a CD34 surface membrane antigen. This antigen is used for purification, e.g., on affinity columns which bind CD34. After the bone marrow is harvested, the mononuclear cells are separated from the other components by means of ficol gradient centrifugation. This is performed by a semi-automated method using a cell separator (e.g., a Baxter Fenwal CS3000+ or Terumo machine). The light density cells, composed mostly of mononuclear cells are collected and the cells are incubated in plastic flasks at 37° C. for 1.5 hours. The adherent cells (monocytes, macrophages and B-Cells) are discarded. The non-adherent cells are then collected and incubated with a monoclonal anti-CD34 antibody (e.g., the murine antibody 9C5) at 4° C. for 30 minutes with gentle rotation. The final concentration for the anti-CD34 antibody is 10 μg/ml. After two washes, paramagnetic microspheres (Dyna Beads, supplied by Baxter Immunotherapy Group, Santa Ana, Calif.) coated with sheep antimouse IgG (Fc) antibody are added to the cell suspension at a ratio of 2 cells/bead. After a further incubation period of 30 minutes at 4° C., the rosetted cells with magnetic beads are collected with a magnet. Chymopapain (supplied by Baxter Immunotherapy Group, Santa Ana, Calif.) at a final concentration of 200 U/ml is added to release the beads from the $CD34^+$ cells. Alternatively, and preferably, an affinity column isolation procedure can be used which binds to CD34, or to antibodies bound to CD34 (see, the examples below). See, Ho et al. (1995) *Stem Cells* 13 (suppl. 3): 100–105. See also, Brenner (1993) *Journal of Hematotherapy* 2: 7–17.

In another embodiment, hematopoetic stem cells are isolated from fetal cord blood. Yu et al. (1995) *PNAS* 92: 699–703 describe a preferred method of transducing $CD34^+$ cells from human fetal cord blood using retroviral vectors.

Ex vivo Transformation of T Cells

Rather than using stem cells, T cells are also used in preferred embodiments in ex vivo procedures. Several techniques are known for isolating T cells. In one method, Ficoll-Hypaque density gradient centrifugation is used to separate PBMC from red blood cells and neutrophils according to established procedures. Cells are washed with modified AIM-V (which consists or AIM-V (GIBCO) with 2 mM glutamine, 10 µg/ml gentamicin sulfate, 50 µg/ml streptomycin) supplemented with 1% fetal bovine serum (FBS). Enrichment for T cells is performed by negative or positive selection with appropriate monoclonal antibodies coupled to columns or magnetic beads according to standard techniques. An aliquot of cells is analyzed for desired cell surface phenotype (e.g., CD4, CD8, CD3, CD14, etc.).

Cells are washed and resuspended at a concentration of $5\times10^5$ cells per ml of AIM-V modified as above and containing 5% FBS and 100 U/ml recombinant IL-2 (rIL-2) (supplemented AIM-V). Where the cells are isolated from and HIV+ patient, 25 nM CD4-PE40 (a recombinant protein consisting of the HIV-1-binding CD4 domain linked to the translocation and ADP-ribosylation domains of *Pseudomonas aeruginosa* exotoxin A) is optionally added to the cell cultures for the remainder of the cell expansion to selectively remove HIV infected cells from the culture. CD4-PE40 has been shown to inhibit p24 production in HIV-1-infected cell cultures and to selectively kill HIV-1-infected cells.

To stimulate proliferation, OKT3 monoclonal antibody (Ortho Diagnostics) is added to a concentration of 10 ng/ml and the cells are plated in 24 well plates with 0.5 ml per well. The cells are cultured at 37° C. in a humidified incubator with 5% $CO_2$ for 48 hours. Media is aspirated from the cells and 1 ml of vector-containing supernatant (described below) supplemented with 5 µl/ml of protamine sulfate, 100 U/ml rIL-2, 100 U/ml penicillin, 0.25 µg/ml amphotericin B/ml and an additional 100 µg/ml streptomycin (25 nM CD4-PE40 can be added as described above).

The expression of surface markers facilitates identification and purification of T cells. Methods of identification and isolation of T cells include FACS, column chromatography, panning with magnetic beads, western blots, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like. For a review of immunological and immunoassay procedures in general, see Stites and Terr (eds.) 1991 *Basic and Clinical Immunology* (7th ed.) and Paul supra. For a discussion of how to make antibodies to selected antigens see, e.g. Coligan (1991) Current Protocols in Immunology Wiley/Greene, NY; and Harlow and Lane (1989) *Antibodies: A Laboratory Manual* Cold Spring Harbor Press, NY; Stites et al. (eds.) Basic and Clinical Immunology (4th ed.)

In addition to the ex vivo uses described above, the packaging cell lines of the invention and the HIV packageable nucleic acids of the invention are useful generally in cloning methods. Packageable nucleic acids are packaged in an HIV particle and used to transform an HIV-infectible cell (e.g., a CD4+ cell) in vitro or in vivo. This provides one of skill with a technique for transforming cells with a nucleic acid of choice, e.g., in drug discovery assays, or as a tool in the study of gene regulation.

In Vivo Transformation

HIV particles containing therapeutic nucleic acids can be administered directly to the organism for transduction of cells in vivo. Administration is by any of the routes normally used for introducing a molecule into ultimate contact with blood or tissue cells. Packageable nucleic acids packaged in HIV particles are used to treat and prevent virally-mediated diseases such as AIDS in patients. The packaged nucleic acids are administered in any suitable manner, preferably with pharmaceutically acceptable carriers. Suitable methods of administering such packaged nucleic acids in the context of the present invention to a patient are available, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

The packaged nucleic acids, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the packaged nucleic acid with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Parenteral administration and intravenous administration are the preferred methods of administration. The formulations of packaged nucleic acid can be presented in unit-dose or multi-dose sealed containers, such as ampules and vials. The packaged nucleic acids are not freeze-dried (lyophilized) because HIV particles are destroyed by lyophilization.

Injection solutions and suspensions can be prepared from sterile powders, granules, and tablets of the kind previously described. Cells transduced by the packaged nucleic acid as described above in the context of ex vivo therapy can also be administered intravenously or parenterally as described above.

The dose administered to a patient, in the context of the present invention should be sufficient to effect a beneficial therapeutic response in the patient over time, or to inhibit infection by a pathogen. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of virally-mediated diseases such as AIDS, the physician evaluates circulating plasma levels, vector toxicities, progression of the disease, and the production of anti-vector antibodies. In general, the dose equivalent of a naked nucleic acid from a vector is from about 1 μg to 100 μg for a typical 70 kilogram patient, and doses of vectors which include a retroviral particle are calculated to yield an equivalent amount of inhibitor nucleic acid.

In the practice of this invention, compositions can be administered, for example, by intravenous infusion, orally, topically, intraperitoneally, intravesically or intrathecally. The preferred method of administration will often be oral, rectal or intravenous, but the vectors can be applied in a suitable vehicle for the local and topical treatment of virally-mediated conditions. The vectors of this invention can supplement treatment of virally-mediated conditions by any known conventional therapy, including cytotoxic agents, nucleotide analogues and biologic response modifiers.

For administration, inhibitors and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

Prior to infusion, blood samples are obtained and saved for analysis. Between $1\times10^8$ and $1\times10^{12}$ transduced cells are infused intravenously over 60–200 minutes. Vital signs and oxygen saturation by pulse oximetry are closely monitored. Blood samples are obtained 5 minutes and 1 hour following infusion and saved for subsequent analysis. Leukopheresis, transduction and reinfusion are repeated every 2 to 3 months for a total of 4 to 6 treatments in a one year period. After the first treatment, infusions can be performed on a outpatient basis at the discretion of the clinician. If the reinfusion is given as an outpatient, the participant is monitored for at least 4, and preferably 8 hours following the therapy.

Transduced cells are prepared for reinfusion according to established methods. See, Abrahamsen et al. (1991) *J. Clin. Apheresis* 6:48–53; Carter et al. (1988) *J. Clin. Arpheresis* 4:113–117; Aebersold et al. (1988), *J. Immunol. Methods* 112: 1–7; Muul et al. (1987) *J. Immunol. Methods* 101:171–181 and Carter et al. (1987) *Transfusion* 27:362–365. After a period of about 2–4 weeks in culture, the cells should number between $1\times10^8$ and $1\times10^{12}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent.

If a patient undergoing infusion of a vector or transduced cell develops fevers, chills, or muscle aches, he/she receives the appropriate dose of aspirin, ibuprofen or acetaminophen. Patients who experience reactions to the infusion such as fever, muscle aches, and chills are premedicated 30 minutes prior to the future infusions with either aspirin, acetaminophen, or diphenhydramine. Meperidine is used for more severe chills and muscle aches that do not quickly respond to antipyretics and antihistamines. Cell infusion is slowed or discontinued depending upon the severity of the reaction.

HIV Vectors

The present application provides stable packaging systems for gene transfer using an HIV-1 packaging cell line and high titers of HIV-based vectors. HIV based vectors specifically deliver genes into $CD4^+$ T cells and non-dividing cells such as terminally differentiated macrophages. In addition, packaging of a therapeutic gene in an HIV core ensures its cellular entry through the same cell compartments as its target, and increases its efficiency. Optional inclusion of portions of the RRE targeting element further aids in colocalization of a therapeutic vector and HIV target.

Figure 7:
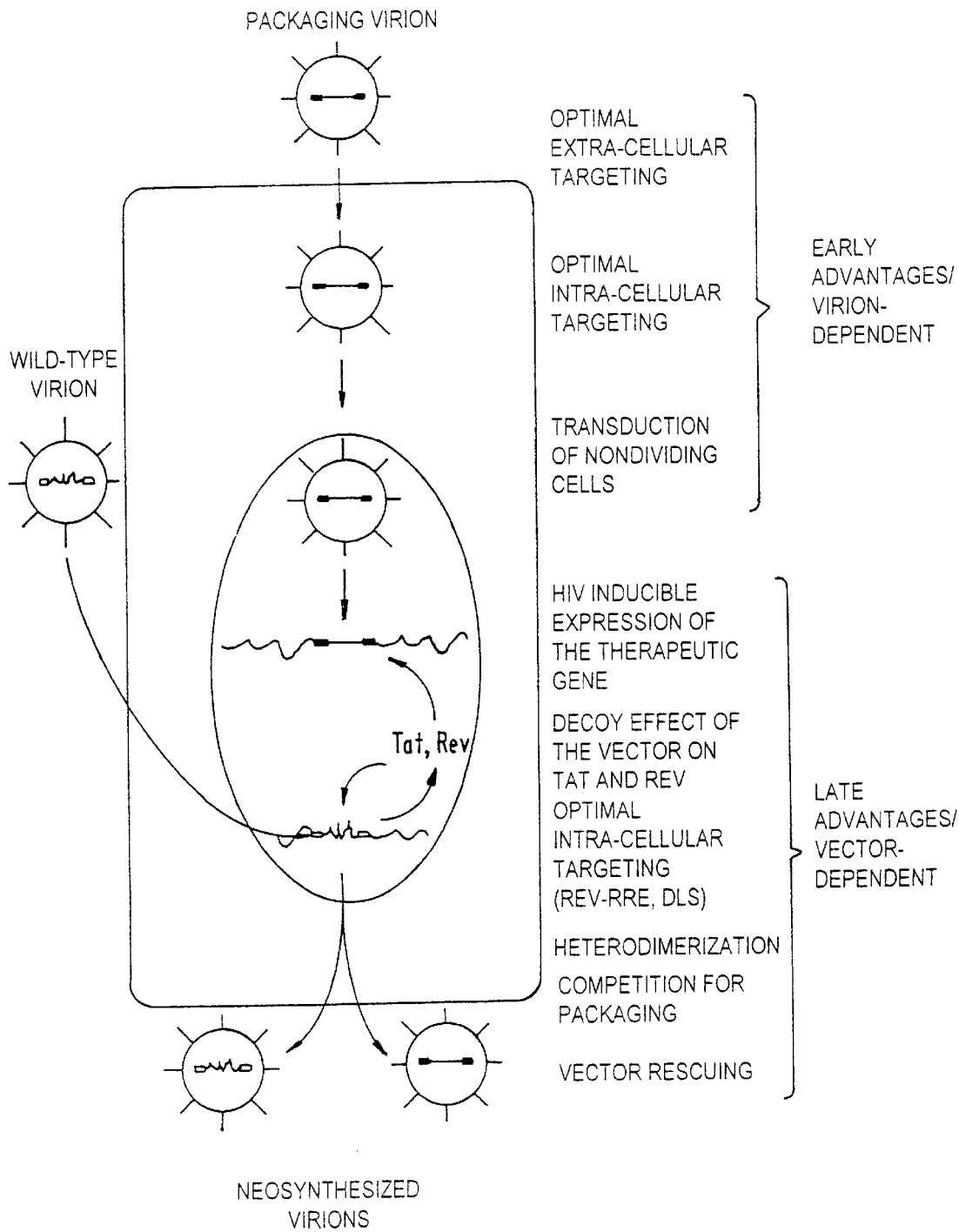
FIG. 7 is a schematic drawing depicting certain advantages to HIV-based anti-viral vectors.

Besides these remarkable targeting abilities due to virion components, an HIV-derived gene delivery has other advantages linked to vector components (FIG. 7). These advantages occur, e.g., after transgene integration and during wild-type HIV infection of the transduced cell. The first of these advantages is that expression of vector LTR-driven antiviral genes can be restricted to HIV-infected cells through tat regulation. Once an HIV vector is activated by wild-type HIV regulatory proteins, vector RNA and genomic RNA competes for dimerization and for packaging. HIV vectors typically contain, upstream of the 5' splice donor site, a region named the dimer linkage structure (DLS) involved in dimerization of HIV RNA strands. In particular, the first loop of the main packaging signal is able to induce the formation of homo- or heterodimers through a "kissing-loop" interaction. Therefore, HIV vector RNA can dimerize with HIV genomic RNA so that vector/genomic RNA heterodimers are encapsidated in budding particles. Such hybrid virions are less infectious because of a block in strand transfers during reverse transcription and/or as a result of the production of defective recombinants. Thus, a vector DLS interferes with the replicative cycle of HIV in transduced cells. Moreover, by interacting with the HIV genomic RNA DLS, the vector DLS can colocalize both RNAs. This colocalization improves the cleavage efficiency of the viral RNA by an anti-HIV ribozymes (discussed supra) inserted in the vector. HIV vectors also contain the main packaging signal (psi site). Therefore, they compete with wild-type HIV genomic RNA for packaging into neosynthesized virions during productive infection of transduced cells. During infection of transduced cells, neosynthesized viral particles package vector RNA. This way, they carry and propagate the vector RNA to cells infected during the HIV infection cycle. In vivo, this is a major advantage for an HIV-derived system of gene transfer (FIG. 7).

HIV vectors interfere with wild-type HIV infection through other mechanisms as well. HIV vectors can have a TAR and/or RRE decoy effect on wild-type tat and/or rev, and reduce the infection of transduced cells.

Viral Inhibitors

As shown in the examples herein, HIV vectors have anti-HIV activity per se. For example, the regulatory and packaging elements common to such vectors act as molecular decoys for HIV regulatory proteins. For example, vectors comprising TAR sequences act as tat decoys, and vectors comprising RRE sequences act as Rev decoys. HIV packaging sites found in HIV-based vectors acts as a decoy for HIV packaging elements.

Specialized viral inhibitors are also typically encoded by the packaged nucleic acids of the invention. Thus, techniques applicable to the construction and maintenance of nucleic acids apply to the inhibitors of the present invention. Anti-viral agents which are optionally incorporated into the viral inhibitors of the invention include anti-sense genes, ribozymes, decoy genes, and transdominant nucleic acids.

An antisense nucleic acid is a nucleic acid that, upon expression, hybridizes to a particular RNA molecule, to a transcriptional promoter or to the sense strand of a gene. By hybridizing, the antisense nucleic acid interferes with the transcription of a complementary nucleic acid, the translation of an mRNA, or the function of a catalytic RNA. Antisense molecules useful in this invention include those that hybridize to viral gene transcripts. Two target sequences for antisense molecules are the first and second exons of the HIV genes tat and rev. Chatterjee and Wong, supra, and Marcus-Sekura (*Analytical Biochemistry* (1988) 172, 289–285) describe the use of anti-sense genes which block or modify gene expression.

A ribozyme is a catalytic RNA molecule that cleaves other RNA molecules having particular nucleic acid sequences. General methods for the construction of ribozymes, including hairpin ribozymes, hammerhead ribozymes, RNAse P ribozymes (i.e., ribozymes derived from the naturally occurring RNAse P ribozyme from prokaryotes or eukaryotes) are known in the art. Castanotto et al (1994) *Advances in Pharmacology* 25: 289–317 provides and overview of ribozymes in general, including group I ribozymes, hammerhead ribozymes, hairpin ribozymes, RNAse P, and axhead ribozymes. Ribozymes useful in this invention include those that cleave viral transcripts, particularly HIV gene transcripts. Ojwang et al., *Proc. Nat'l. Acad. Sci., U.S.A.*, 89:10802–06 (1992); Wong-Staal et al. (PCT/US94/05700); Ojwang et al. (1993) *Proc Natl Acad Sci USA* 90:6340–6344; Yamada et al. (1994) Human Gene Therapy 1:39–45; Leavitt et al. (1995) *Proc Natl Acad Sci USA* 92:699–703; Leavitt et al. (1994) *Human Gene Therapy* 5:1151–1120; Yamada et al. (1994) *Virology* 205:121–126, and Dropulic et al. (1992) *Journal of Virology* 66(3):1432–1441 provide an examples of HIV-1 specific hairpin and hammerhead ribozymes.

Briefly, two types of ribozymes that are particularly useful in this invention include the hairpin ribozyme and the hammerhead ribozyme. The hammerhead ribozyme (see, Rossie et al. (1991) *Pharmac. Ther.* 50:245–254; Forster and Symons (1987) *Cell* 48:211–220; Haseloff and Gerlach (1988) *Nature* 328:596–600; Walbot and Bruening (1988) Nature 334:196; Haseloff and Gerlach (1988) *Nature* 334:585; and Dropulic et al and Castanotto et al., and the references cited therein, supra) and the hairpin ribozyme (see, e.g., Hampel et al. (1990) *Nucl. Acids Res.* 18:299–304; Hempel et al., (1990) European Patent Publication No. 0 360 257; U.S. Pat. No. 5,254,678, issued Oct. 19, 1993; Wong-Staal et al., PCT/US94/05700; Ojwang et al. (1993) *Proc Natl Acad Sci USA* 90:6340–6344; Yamada et al. (1994) Human Gene Therapy 1:39–45; Leavitt et al. (1995) *Proc Natl Acad Sci USA* 92:699–703; Leavitt et al. (1994) *Human Gene Therapy* 5:1151–1120; and Yamada et al. (1994) *Virology* 205:121–126) are catalytic molecules having antisense and endoribonucleotidase activity. Intracellular expression of hammerhead ribozymes and a hairpin ribozymes directed against HIV RNA has been shown to confer significant resistance to HIV infection. These ribozymes are constructed to target a portion of the HIV genome, or nucleic acid encoded by the genome. Preferred target sites in HIV-1 include the U5 region, and the polymerase gene.

The typical sequence requirement for cleavage by a hairpin ribozyme is an RNA sequence consisting of NNNG/CN*GUCNNNNNNNN (SEQ ID NO:2)(where N*G is the cleavage site, and where N is any of G, U, C, or A). The sequence requirement at the cleavage site for the hammerhead ribozyme is an RNA sequence consisting of NUX (where N is any of G, U, C, or A and X represents C, U or A). Accordingly, the same target within the hairpin leader sequence, GUC, is targetable by the hammerhead ribozyme. The additional nucleotides of the hammerhead ribozyme or hairpin ribozyme which mediate sequence specificity, are determined by the common target flanking nucleotides and the hammerhead and hairpin consensus sequences.

A decoy nucleic acid is a nucleic acid having a sequence recognized by a regulatory nucleic acid binding protein (i.e., a transcription factor, cell trafficking factor, etc.). Upon expression, the transcription factor binds to the decoy nucleic acid, rather than to its natural target in the genome. Useful decoy nucleic acid sequences include any sequence to which a viral transcription factor binds. For instance, the TAR sequence, to which the tat protein binds, and the HIV RRE sequence (in particular the SL II sequence), to which the rev proteins binds are suitable sequences to use as decoy nucleic acids.

A transdominant nucleic acid is a nucleic acid which expresses a protein whose phenotype, when supplied by transcomplementation, will overcome the effect of the native form of the protein. For example, tat and rev can be mutated to retain the ability to bind to TAR and RRE, respectively, but to lack the proper regulatory function of those proteins. In particular, rev can be made transdominant by eliminating the leucine-rich domain close to the C terminus which is essential for proper normal regulation of transcription. Tat transdominant proteins can be generated by mutations in the RNA binding/nuclear localization domain. Reciprocal complementation of defective HIV molecular clones is described, e.g., in Lori et al. (1992) *Journal of Virology* 66(9) 5553–5560.

EXAMPLES

The following examples are provided by way of illustration only and not by way of limitation. Those of skill will readily recognize a variety of noncritical parameters which could be changed or modified to yield essentially similar results.

Materials and Methods

Figure 2:
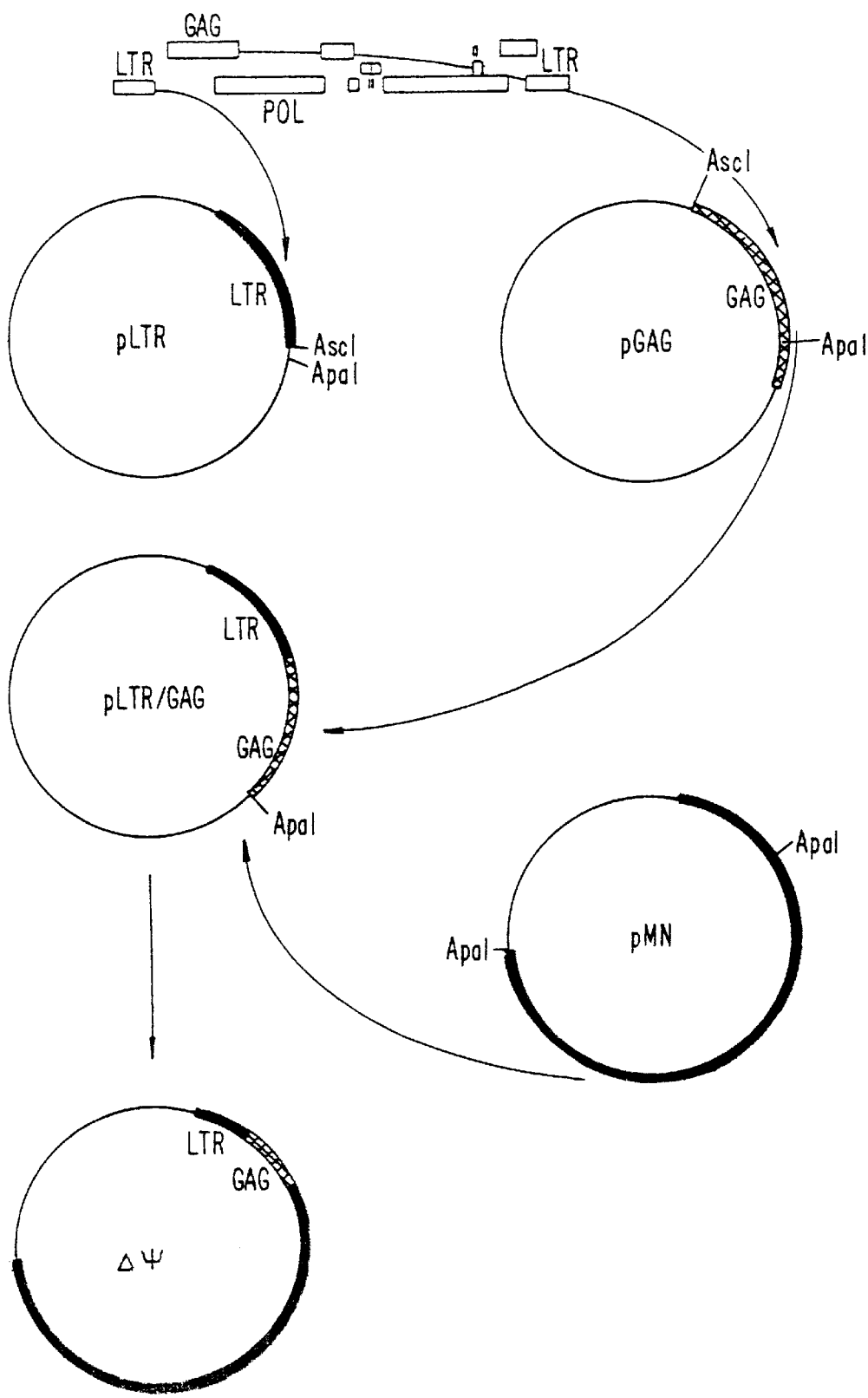
FIG. 2 is a diagram of the construction of the $\Delta\Psi$ packaging plasmid.

The following materials and methods were used in the examples below. Packaging plasmid construction. The HIV-1-MN-ST.1 genome (Lori, et al. (1992) *J. Virol.* 66(9): 5553–5560) was cloned into the commercial PCR™ 11 vector (Invitrogen, San Diego, Calif.). To delete the major packaging site (FIG. 1), the first 743 bases of the HIV-1-MN LTR (nucleotide numbering according to G. Myers et al., Eds. (1992) *Human Retroviruses and AIDS* Los Alamos National Laboratory, Los Alamos, N. Mex.; a compilation and analysis of nucleic acid and amino acid sequences) were amplified by PCR introducing an Ascl restriction site at the 3' end of the PCR product by using the following oligomers: 5' oligo: TGGATGGGTTAATTTACTCCC (SEQ ID NO:3); 3' oligo: GGCGCGCCTCACCAGTCGCCGCCCC (SEQ ID NO:4). This PCR product was cloned in the PCR 11 vector which contains a unique Apa I restriction site (plasmid pLTR, FIG. 2). Then a gag-pol fragment (from nucleotide 1 in gag to nucleotide 360 in pol) was amplified, introducing an AscI restriction site at the 5' end of the PCR fragment by using the following oligomers: 5' oligo: GGGGCGCGCCGAGAGAGATGGGGTGC-GAGAGCGTCGG (SEQ ID NO:5); 3' oligo: CTGATCAT-ACTGTCTTACTTTG (SEQ ID NO:6). The resulting PCR fragment containing a unique ApaI restriction site was cloned into the PCR 11 vector (plasmid pGAC). Plasmids pLTR and pGAG were digested by AscI and ApaI and the AscI-ApaI fragment of pGAG, corresponding to the 1230 first bases of gag was inserted in the pLTR clone (plasmid pLTR/GAG). Thus, 37 bases, starting from 6 bases downstream the 5' major splice donor to 7 bases upstream of the beginning of gag (FIG. 1), were deleted in the pLTR/GAG construct. Finally an ApaI-ApaI fragment of the parental pMN clone corresponding to the viral genome downstream from the ApaI site in gag was inserted in pLTR/GAG to generate the plasmid Δψ.

Packaged plasmid construction. The vector V653gpt (FIG. 1) was obtained by replacement of the neomycin phosphotransferase (neo$^r$) gene on the previously described V653RSN plasmid (Parolin, et al. (1994) *J. Virol.* 68(6):3888–3895) with the xanthine-guanine phosphoribosyl transferase (gpt) gene. The gpt gene was amplified by PCR introducing an XhoI site at the 5' end and a SalI site at the 3' end of the PCR product by using the following oligomers: 5'oligo: CCGCTCGAGATGAGCGAAAAATACATCGTC (SEQ ID NO:7); 3'oligo: CGGTCGACTTAGCGGCCGC-GACCGGAGATTGGCGGG (SEQ ID NO:8). V653RSN was digested with SalI, which recognizes 2 sites in the sequences flanking the neo$^r$ gene, and ligated with the PCR product digested with XhoI and SalI.

RT activity assay. To measure viral Reverse Transcriptase (RT) activity, culture supernatant (0.50 ml) was mixed with 0.24 ml 30% polyethylene glycol and 20 μl 4M NaCl, and microcentrifuged at 14,000 rpm for 30 min. The pellet was resuspended in 10 mM Tris-HCl pH 7.8, 100 mM NaCl, 1 mM EDTA, 0.1% Triton X100, and 40 μl of a mixture containing 62.5 mM Tris-HCl pH 7.8, 25 mM $MgCl_2$, 25 mM KCl, 2.5 mM dithiothreitol, 31.25 μg/ml poly(rA) xoligo(dT) 12–18 (Pharmacia), 62.5 μCi/6.25 nmole/ml of ($^3$H)dTTP. After a one-hour incubation at 37° C. the mixture was spotted on DE81 paper (Whatman, Maidstone, UK), air-dried, washed three times with 5% sodium pyrophosphate and twice more with water, and air-dried again. Radioactivity was measured by a scintillation spectrometer (Beckman, Fullerton, Calif.).

RT-PCR assay. Before HIV RNA detection, cell culture supernatant was treated with DNAse I (Boehringer Mannheim, Indianapolis, Ind.) for one hour (500 μl containing 10 U of enzyme and 50 μl of 200 mM TrisHCl (pH 8.3), 500 mM KCl, 25 mM $MgCl_2$, 1 mg/ml bovine serum albumin). Then 500 μl of 6M guanidine thiocyanate, 50 mM Tris-HCl, and 5 μl of glass milk (GENECLEAN 11, B10101, Vista, Calif.) was added, and the mixture was rotated for 90 min. at 20° C. After 3 washings, the RNA in the pellet was air-dried and eluted with 5 μl of water for 3 min. at 50° C. To this 5 μl of RNA, 2 U of Tth DNA polymerase and 1 μl of 10× RT buffer (Boehringer), 0.8 μg HIV gag oligonucleotide SK39, and 1 μl of 2 mM dNTP were added. The RNA in this mixture was then reverse transcribed (4.5 μl of the mixture and 0.5 μl of 9 mM $MnCl_2$ incubated 20 min. at 65° C.). As a control a reaction was run without $MnCl_2$ (4.5 μl of the mixture and 0.5 μl of water on ice for 20 min.). Finally, for the PCR, 2 μl of 10× PCR buffer (Boehringer), 2.5 μl of 7.5 mM EGTA, 12.5 μl of $H_2O$, 0.8 μG HIV gag oligonucleotide SK38, and 2 μl of 2 mM dNTP were added. After 5 min. at 94° C., 30 cycles were performed: denaturation for 1 min. at 94° C., hybridization for 1 min. at 52° C., and polymerization for 30 seconds at 72° C. The amplified products were run in a 2% agarose gel, blotted onto a GENESCREENPLUS nylon membrane (NEN Research Products, Boston, Mass.) by salt transfer, and hybridized with an α-32P-labeled (RANDOM PRIMED DNA LABELING kit, Boehringer) HIV-1 gag fragment. Labeled RT-PCR fragments were visualized by autoradiography.

Infectivity assay. To determine the infectivity of HIV-1 virions, serial dilutions of culture supernatants were incubated in quadruplicate with $4 \times 10^4$ Molt4/8 cells in 200 μl RPMI-10% FCS, cultured for 13 days, washed, and then cultured for an additional day. The percentage of cultures positive for HIV-1 p24 assay was then determined for each viral input.

Transduction. g cell (cells expressing an HIV packageable RNA) supernatants were filtered (pore size 0.22 μm), diluted 1:10, and added for 24 hours to 30% confluent Hela T4 cells cultivated in 1 ml DMEM-10% FCS (6-well plate, Costar). Two days later, the HelaT4 cells were selected in DMEM supplemented with 10% dialyzed FCS, 250 μg/ml xanthine, 15 μg/ml hypoxanthine, 10 μg/ml thymidine, 2 μg/ml aminopterin, 25 μg/ml mycophenolic acid, and 150 μg/ml of L-glutamine. After 4 weeks, resistant cells were counted under an inverted optical microscope.

PCR detection of the transduced vector. Genomic DNA was extracted using the QIAAMP BLOOD kit (QIAGEN, Chatsworth, Calif.). PCR was performed on 200 ng DNA of transduced HelaT4 cells or ψ422 cells (negative control), or on 2 pg of V653gpt plasmid mixed with 200 ng DNA of HelaT4 cells (positive control). A first LTR-RRE fragment of the vector was amplified using the following oligomers: 5'oligo: TTTTCGCGAGCGGCCGCCG-GAAGGGCTAATTCACTCC (SEQ ID NO:9), 3'oligo: GGTATCTTTCCACAGCTAGG (SEQ ID NO:10); a second RRE-gpt fragment using the oligomers: 5'oligo: GGAGCTTTGTTCCTTGGG (SEQ ID NO:11), 3' oligo: ATCAACCAGCGGACGACCAG (SEQ ID NO:12); and a third gpt-LTR fragment using the oligomers: 5'oligo: AGC-TACGATCACGACAACCA (SEQ ID NO:13), 3' oligo: TTTTCGCGAGCGGCCGCTGCTA-GAGATTTCCACACTG (SEQ ID NO:14). To 5 μl of cellular DNA, 0.4 μg of each oligomer, 2.5 μl of 2 mM dNTP, 2.5 μl of 25 mM $MgCl_2$, 0.5 U of Taq DNA polymerase and 2.5 μl of 10× PCR buffer (Promega, Madison, Wis.), and water for a final volume of 25 μl were added. After 5 min. at 94° C., 35 cycles were performed: denaturation for 1 min. at 94° C., hybridization for 1 min. at 60° C., and polymerization for 2 min. 30 seconds at 72° C. The PCR fragments were then analyzed as described for the RT-PCR assay, the LTR-RRE and the gpt-LTR fragments being hybridized with an HIV-LTR probe, and the RRE-gpt fragment with a gpt probe.

RIPA. Ten million cells were washed with PBS, incubated one hour in cysteine-free DMEM-10% FCS, and then labelled for 5 hours by the addition of 10 μl of L-$^{35}$S cysteine (11 mCi/0.0102 μmol/ml). The cells were washed again with PBS and lysed in 2 ml of 5 mM Tris (pH 8.0), 150 mM NaCl, 10 mM EDTA, 0.1% SDS, 1 mM PMSF, 1% TritonX100, 1% deoxycholic acid. After an one-hour incubation at 4° C., the lysate was microcentrifuged for 30 min. at 14,000 rpm. One ml of supernatant was added to 6 µg of protein A sepharose (CL-4B, Pharmacia LKB, Uppsala, Sweden) that had been preincubated with 10 µl of a pool of human HIV+plasma. After 18 hours of incubation at 4° C., the sepharose was washed, boiled for 10 min., and microcentrifuged. Twenty-five µl of the supernatant was then run on an SDS-PAGE gel. After electrophoresis, the gel was dried and autoradiographied.

Example 1
A Stable HIV-1 Packaging Cell Line

The HIV-1$_{MN}$ST.1 molecular clone was chosen as the base clone for making a packaging cell line because of its efficiency of infection in both monocytes and T-cells (Lori, et al. (1992) *J. Virol.* 66(9):5553–5560). The packaging vector Δψ was constructed by deleting 37 bases between the major splice donor site and the beginning of the gag gene (FIG. 1), a sequence within the previously defined major packaging site for HIV-1 (Lever, et al. (1989) *J. Virol.* 63(9):4085–4087; Aldovini, et al. (1990) *J. Virol.* 64(5):1920–1926; Clavel, et al. (1990) *J. Virol.* 64(10):5230–5234; Poznansky, et al. (1991) *J. Virol.* 65:532–536; Hayashi, et al. (1992) *Virology* 188:590–599). For this deletion, PCR fragments derived from the LTR and gag were first ligated to each other, and then subsequently ligated with the rest of the viral genome to generate the Δψ clone (see, Methods and FIG. 2). Δψ was used to generate an HIV-1 packaging line. For this purpose, Hela cells were cotransfected with Δψ and a plasmid containing the neo$^r$ gene and cultured in the presence of neomycin (G418).

The Hela cells were transfected by the Calcium-Phosphate method. A subconfluent Hela culture in a 6-well plate (Costar, Cambridge, Mass.) was transfected with linearized and Calcium-Phosphate precipitated plasmid Δ$_\gamma$ (10 µg) and plasmid SV-NEO containing the neo$^r$ gene driven by the SV40 promotor (0.6 µg) in Dulbecco's modified Eagle's medium supplemented with 10% FCS, antibiotics and glutamine (DMEM-10% FCS). After 18 hours, wells were washed with Dulbecco's phosphate—buffered saline (PBS) pH 7.8, incubated for 2 min. at 20° C. with 15% glycerol solution in HEPES-buffered saline (50 mM HEPES pH 7.1, 280 mM NaCl, 1.5 mM Na2HP04), washed twice with PBS and cultured in DMEM-10% FCS. At day 3, 500 µg/ml G418 (Gibco BRL, Grand Island, N.Y.) was added to the cell culture.

Figure 3:
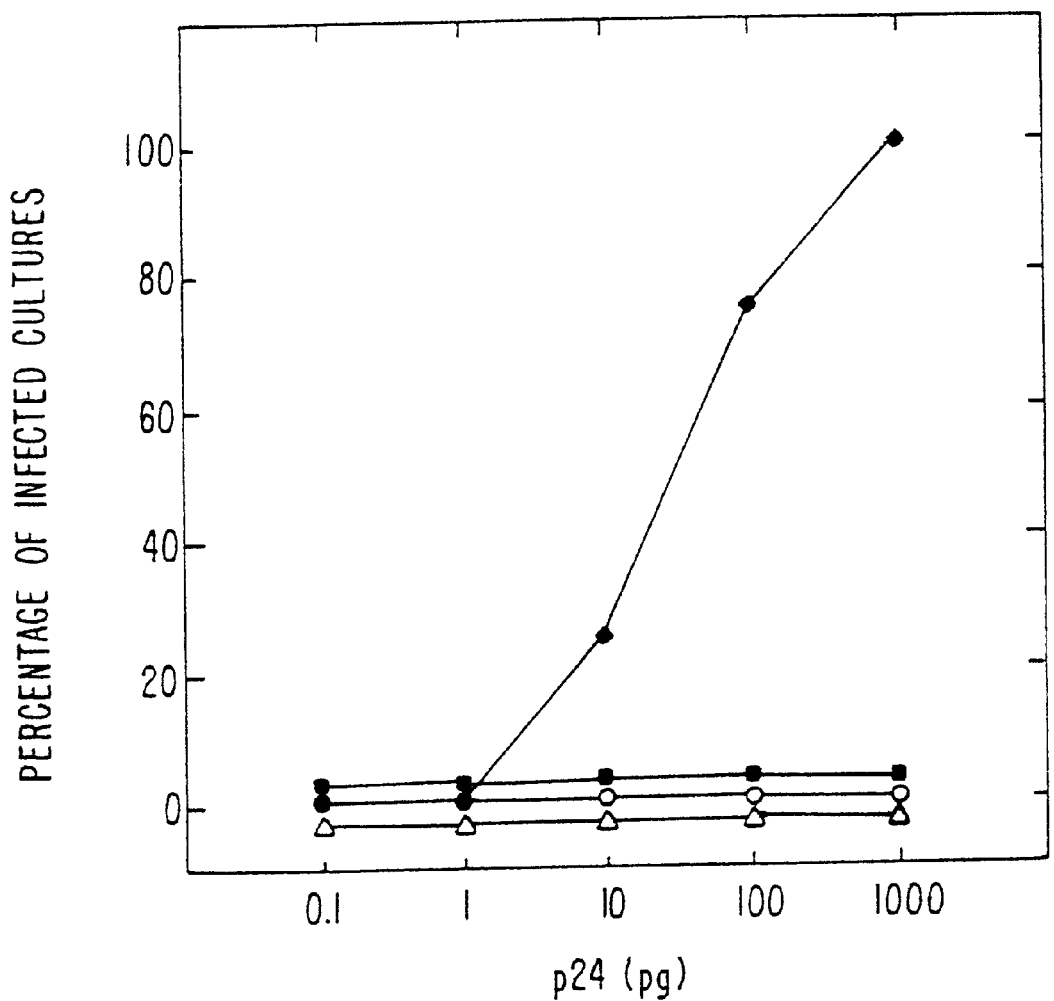
FIG. 3 shows the non-infectivity of the T422 and g cell (packaging cells transduced with a packageable nucleic acid) line supernatants. Quadruplicate cultures of Molt4/8 cells exposed to various amounts (0.1 to 1,000 pg of p24 antigen) of wild type HIV-1-MN (4) or mutant (T422,n; gV,O; gZ,A) virions were tested at day 14 for HIV-1 infection by p24 capture assay. The, percentage of cultures which were HIV p24 positive is represented for each viral input.

A G418-resistant clone, ψ422, which produced 20 ng/ml of p24$^{Gag}$ antigen, as measured in the culture supernatants using a commercial ELISA kit (Coulter, Miami, Fla.), was isolated and further analyzed. This clone was able to induce the formation of syncytia after an overnight coculture with uninfected CD4$^+$ human T-cells Molt4/8 (data not shown). To determine if HIV-1 structural proteins were correctly expressed in the ψ422 cells, the cells were metabolically labeled and the viral proteins immunoprecipitated from the cell lysate. ψ422 cells synthesize the major HIV-1 structural proteins, including the envelope precursor gp160 and the external envelope glycoprotein gp120, the p55 gag immature protein and its p25 subproduct. Electron microscopy showed the production of a large amount of virions by the ψ422 cell line, including many mature particles. These particles contain comparable specific RT activity (4,947 cpm/50 ng p24/ml) to that of wild type MN virions (5,364 cpm/50 ng p24/ml) (see, methods). However, these particles are not infectious, as shown in FIG. 3. CD4$^+$ T-cells Molt4/8 exposed to the equivalent of 1 ng of p24 of ψ422 virions did not express p24 antigen 14 days later. In the same experiment, HIV production was detected in cell cultures exposed to 10 pg of wild type HIV-1-MN virions. The lack of infectivity of the ψ422 viral particles correlated with a reduction in the RNA content in these particles. Viral RNA was not detected by RT-PCR in 140 pg of p24 equivalent of ψ422 virions, whereas HIV RNA was detected in 35 pg of p24 equivalent of wild type MN virions. The ψ422 cell line has been stable in culture for several months, producing 1 to 20 ng/ml p24 equivalent of non-infectious virions.

Example 2
Use of ψ422 Cell Line for Gene Transfer

In addition to the main ψ sequence encompassing the major splice donor site and the beginning of gag, other sequences within the HIV-1 genome play a role in the packaging of viral RNA. The first hundred bases of the gag gene is involved in the binding of the viral RNA to the nucleocapsid of the virion (Buchschacher, et al. (1992) *J Virol.* 66(5):2731–2739; Parolin, et al. (1994) *J. Virol.* 68(6):3888–3895; Luban, et al. (1991) *J. Virol.* 65:3203–3212; Berkowitz, et al. (1993) *J. Virol.* 67(12):71 90–7200; Luban, et al. (1994) *J. Virol.* 68(6):3784–3793). A stretch within the env gene, including the Rev Responsive Element (RRE) has been reported to also contain a packaging signal (Richardson, et al. (1993) *J. Virol.* 67(7):3997–4005; Parolin, et al. (1994) *J. Virol.* 68(6):3888–3895). An HIV-1 vector, V653RSN, containing the first 653 bases of gag and an RRE-containing fragment of env is available (Parolin, et al. (1994) *J. Virol.* 68(6):3888–3895). The neo$^r$ gene in V653RSN was replaced with the gpt gene and transfected this new plasmid, V653gpt, into ψ422 cells. Gpt can serve as a positive selectable marker in media containing mycophenolic acid, an inhibitor of de novo synthesis of guanine monophosphate (Mulligan, et al. (1981) *Proc. Natl. Acad. Sci. USA.* 78(4):2072–2076). Moreover, gpt also serves as a negative selectable marker, a suicide gene, using 8-thioxanthine as a counter selective agent (Spring, et al. (1994) *Biochemica et Biophysica Acta.* 1218:158–162). Mycophenolic acid-resistant cell lines (g lines) were isolated from the transfected ψ422 cells and their filtered supernatants were used to transduce Hela-T4 cells. Transduction efficiency was evaluated 4 weeks later by counting the mycophenolic acid-resistant Hela-T4 cells. After this selection almost all the Hela-T4 cells transduced with plain medium, ψ422 cell supernatant or V653gpt transfected Hela cell supernatant were dead. In contrast, up to 10$^5$ resistant cells were obtained after transduction with 1 ml of two g cell lines supernatants (Table 1). The capacity of these two g cell lines, gV and gZ, to transfer mycophenolic acid resistance was dependent on the presence of the CD4 receptor on target cells. Hela CD4– cells incubated with g cell supernatant died within 3 weeks in the presence of mycophenolic acid (Table 1).

TABLE 1

Transluction Capacity of g Cell Lines

| Cell Supernatant | (Transducing Target Cell | Experiment | Titer units/ml |
|---|---|---|---|
| gV | Hela-T4 | 1 | 1.2 × 10$^4$ |
|  |  | 2 | 1.0 × 10$^4$ |
|  |  | 3 | 4.6 × 10$^4$ |
|  | Hela |  | 0 |

TABLE 1-continued

Transluction Capacity of g Cell Lines

| Cell Supernatant | (Transducing Target Cell | Experiment | Titer units/ml |
|---|---|---|---|
| gZ | Hela-T4 | 1 | $1.0 \times 10^4$ |
|  |  | 2 | $1.3 \times 10^4$ |
|  |  | 3 | $1.4 \times 10^5$ |
|  | Hela |  | 0 |

Packaging vectors were examined to determine whether replication competent viruses could arise through recombination between viral sequences in the packaging cell line and the packaged nucleic acid. Infectivity of gV and gZ supernatants was tested on Molt4/8 cells. No trace of viral production was detected even when the culture was inoculated with the highest concentration of virions produced by the g cells (FIG. 3).

To determine if the transfer of the $neo^r$ gene was accomplished without rearrangement, the integrity of the V653gpt vector in the transduced cells was checked by PCR. Three overlapping fragments of the vector were amplified from DNA of transduced cells, blotted and hybridized with specific probes. PCR was also carried out on ψ422 cells as a negative control, and on V653gpt plasmid as a positive control. The size and the specificity of the PCR products demonstrated that the V653gpt vector was transferred without modification.

Example 3
Construction of an HIV-2 Based Gene Delivery System

Unlike most retroviruses, HIV is able to infect and replicate in nondividing cells (e.g. monocytes) in the absence of DNA synthesis. Therefore, gene delivery with an HIV vector for HIV infection has a distinct advantage over standard murine retroviral vectors. Use of an HIV-derived vector is also desirable for gene therapy for HIV infection and AIDS, since the packaging signal in the vector RNA is recognized by HIV gag proteins in infected cells, with three primary consequences. First, the vector RNA competes with viral RNA for packaging. Second, the vector RNA is rescued and disseminated to a larger pool of potential HIV target cells. Expression of the inhibitory genes is at minimal levels in uninfected cells, alleviating concerns about cellular toxicity. Third, the presence of a packaging signal sequence in a therapeutic RNA transcript (e.g. a ribozyme or anti-sense RNA) allows tracking of the RNA with HIV RNA to the same cellular compartments, increasing efficiency of activity.

Human immunodeficiency virus type 2 (HIV-2)-based retroviral vectors have several desirable features as vehicles for gene therapy. For instance, the vectors have cell specificity, regulated expression, lower homology to HIV-1 than HIV-1 vectors (preventing homologous recombination to form pathogenic strains of HIV) and attenuated cytopathicity (the latency period for HIV-2 is typically about two to ten times that of HIV-1).

Packaging of HIV-2 vectors depends on efficient packaging of RNA into retroviral particles, which is mediated by a cis-acting sequence element called the packaging signal or "psi" site (ψ). For most retroviruses, including HIV-1 and HIV-2, the principal part of this element is located between the major splice donor site and the gag initiator codon (AUG) in the leader sequence. In the preferred vector of this example, the vector comprises HIV-2 long-terminal repeats (LTR) the HIV-2 psi-site and an internal pol II promoter driving a selectable marker gene. The HIV-2 based components are derived from HIV-2$_{KR}$ described in U.S. Ser. No. 60/001,441 and on deposit with the ATCC 97234. The complete sequence of HIV-2$_{KR}$ is available from GenBank (Accession No. U22047. The HIV-2$_{KR}$ LTRs do not require Rev for basal transcription, and HIV-2$_{KR}$ exhibits reduced cytopathicity compared to other HIV viral clones.

Figure 4:
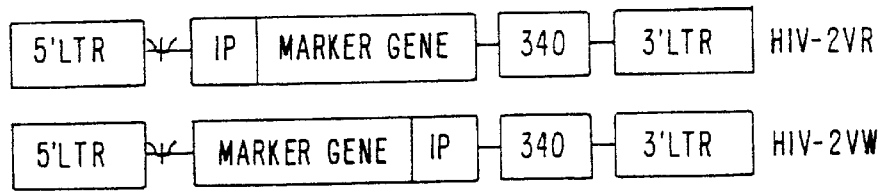
FIG. 4 shows the structure of basic HIV-2 gene delivery vectors. IP indicates an internal promoter; the marker gene is neo or x-gpt. The 340 stands for the MPMV sequence.
Figure 5:
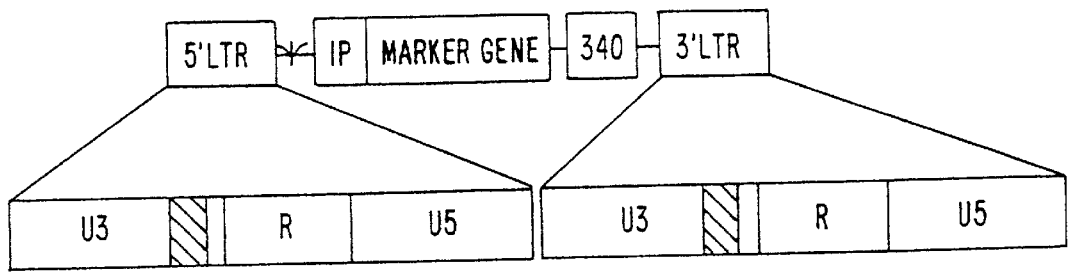
FIG. 5 shows the structure of a rev and rre independent double copy vector. Stripes indicate the inserted pol III promoter and gene cassette.

To ensure Rev independence, the vectors had a 340 bp insert from the Mason Pfizer Monkey Virus (MPMV) inserted into the vector. The insert is sufficient to target nucleic acids to the cytosol in the absence of Rev. See, Bray et al. (1994) *Proc. Natl. Acad. Sci. USA* 91: 1256–1260. The Rev response element (RRE) was deleted. See FIG. 4.

The deletion of the RRE element has an advantage over earlier described HIV vector designs, because RRE expression has been shown to be cytotoxic over time in cells. This design allows for addition of optimum amounts of the gag sequence required for maximum packaging efficiency into the vector construct, because instability sequences (INS) (See, Schwartz et al. (1992) *Journal of Virology* 66:7176–7182) are overwritten by this specific MPMV sequence.

To avoid possible recombination events between the HIV-2 based vector and an HIV-2 based packaging cell line, which can result in wild type HIV-2, the vector was packaged in the HIV-1 packaging cell line ψ-422 described above. The data below shows the rescueability by the HIV-1 packaging cell line, and demonstrates a packaging site decoy effect.

TABLE 2

Transduction capacity of HIV-2 based vector produced on ψ-422 packaging cell line.

| Cell line | supernatant p24 (ng/ml) | Transduction capacity (Transducing particles/ml) |
|---|---|---|
| ψVR 3.4 | 1.2 | 3500 |
| ψVW 4.5.6 | 1.8 | 2100 |

TABLE 3

| Cell Supernatant | Target Cell | Experiment | Titer (TU/ml) |
|---|---|---|---|
| ψ422 | Hela-T4 |  | 0 |
| VR-transfected Hela | Hela-T4 |  | 0 |
| VW-transfected Hela | Hela-T4 |  | 0 |
| ψVR | Hela-T4 | 1 | $0.4 \times 10^4$ |
|  | Hela-T4 | 2 | $1.0 \times 10^4$ |
|  | Hela-T4 | 3 | $2.1 \times 10^4$ |
|  | Hela |  | 0 |
| ψVW | Hela-T4 | 1 | $0.1 \times 10^4$ |
|  | Hela-T4 | 2 | $2.1 \times 10^4$ |
|  | Hela-T4 | 3 | $1.0 \times 10^4$ |
|  | Hela |  | 0 |

Figure 6:
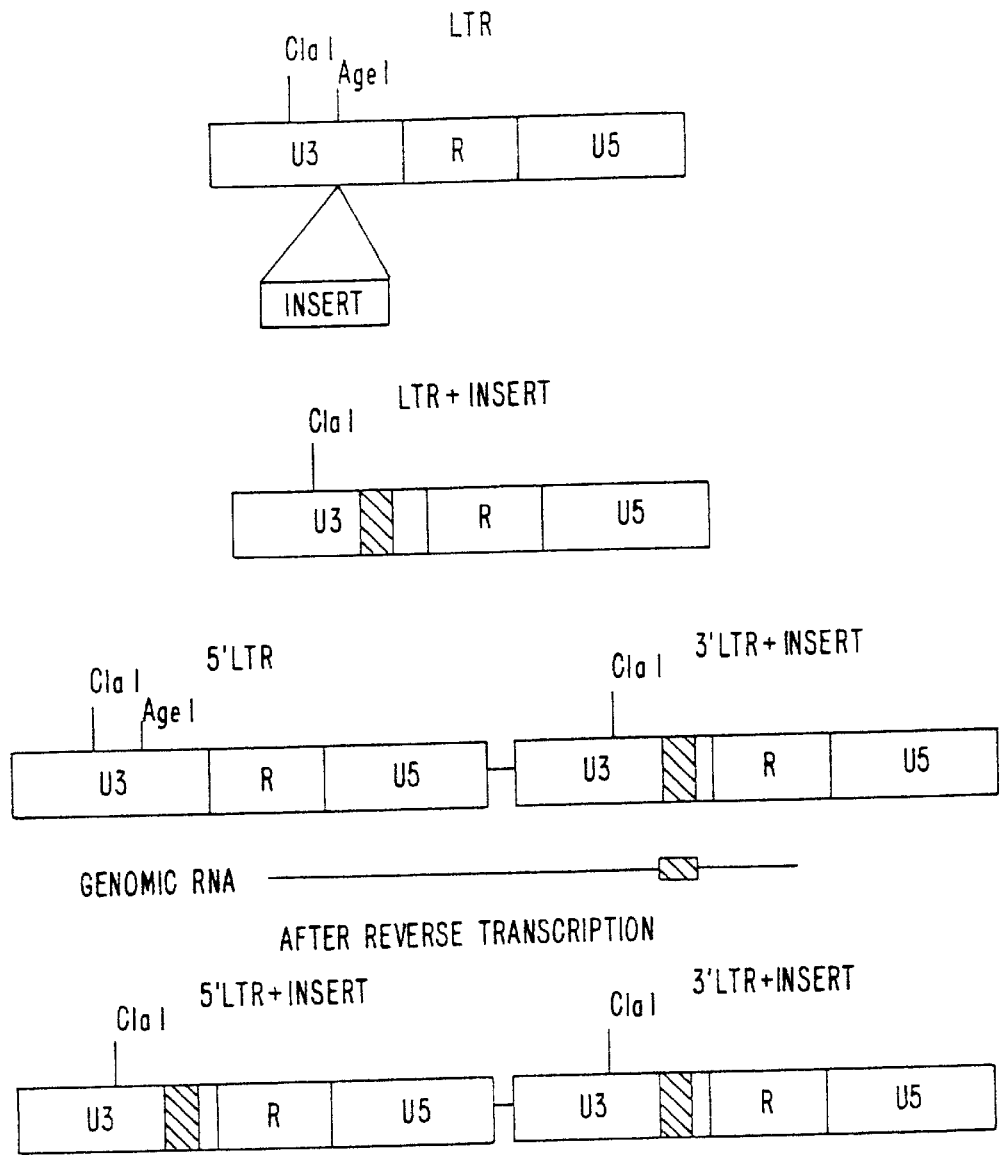
FIG. 6 shows the construction of HIV-2 double copy vectors. pLTR plasmid was digested with Age I and the overhang was filled in. A t-RNAval+Ribozyme cassette was inserted (See, WO 94/26877). The plasmid was digested with Cla I and the insert from the vector was cloned into the Cla I site.

Further improvements to the HIV-2 gene delivery system were also made. A t-RNAval po III promoter was cloned into the U3 region of the 3'LTR for transcription of therapeutic genes such as Ribozymes, RNA-decoys and antisense-RNAs constructs. This design provides a "double copy vector," once the vector genome is reverse transcribed and integrated into the cellular genome. This novel design provides increased RNA levels of the therapeutic genes. See FIG. 6.

This HIV-2-based retroviral vector provides targeted gene delivery and regulated expression of immunogens or antiviral agents in CD4$^+$ cells. Furthermore, it can be pseudotyped by supplying env genes in trans, using the VSV G protein to make the vector able to infect stem cells.

Example 4
Anti-HIV Effects of HIV Based Vectors

After stable transfection with an HIV-1 or HIV-2 vector, ψ422 was shown to synthesize virions able to transduce CD4+ T cells and macrophages, as shown, supra. It was also found that HIV vectors per se, in the absence of a particular antiviral gene, had inhibitory effects on HIV infection of transduced cells.

Using a CAT assay, an RNA transactivation responsive element (TAR) decoy effect of an HIV-1 vector on the viral tat transactivator was monitored, and the consequence of this inhibition evaluated on viral production. Moreover, another HIV-1 vector, which contained the rev responsive element (RRE), had an RRE-decoy effect on the wild type rev protein. These data highlight an advantage of HIV-derived gene delivery systems. Besides improving the targeting into HIV-infectible cells and non-dividing cells, HIV packaged HIV-based vectors have anti-HIV effects, e.g., through interference of vector components with the HIV replicative cycle.

Vectors

The vector V0gpt (FIG. 8, panel a) was generated from the V0SN plasmid (Parolin et al. (1994) *J. Virol.* 68(6):3888–3895) by replacing the neomycin phosphotransferase ($neo^R$) gene with the xanthine-guanine phosphoribosyl transferase (gpt) gene. The gpt gene was amplified by PCR introducing XhoI and SalI sites at the 5' and 3' ends of the PCR product respectively using the oligomers: 5' oligo: CCGCTCGAGATGAGCGAAAAATACATCGTC (SEQ ID NO:7); 3' oligio: CGGTCGACTTAGCGGCCGCGACCG-GAGATTGGCGGG (SEQ ID NO:8). V0SN was deleted of a SalI-SalI fragment containing the $neo^R$ gene, and ligated with the PCR product digested with XhoI and SalI. V653gpt is described supra.

Transfection of the packaging cell line with the HIV vector, infectivity test, transduction, southern blot on transduced cells These assays were performed as described supra and in Corbeau et al. (1996) *Proc. Natl. Acad. Sci. USA* 93:14070–14075.

Plasmids used in CAT assay

Figure 8:
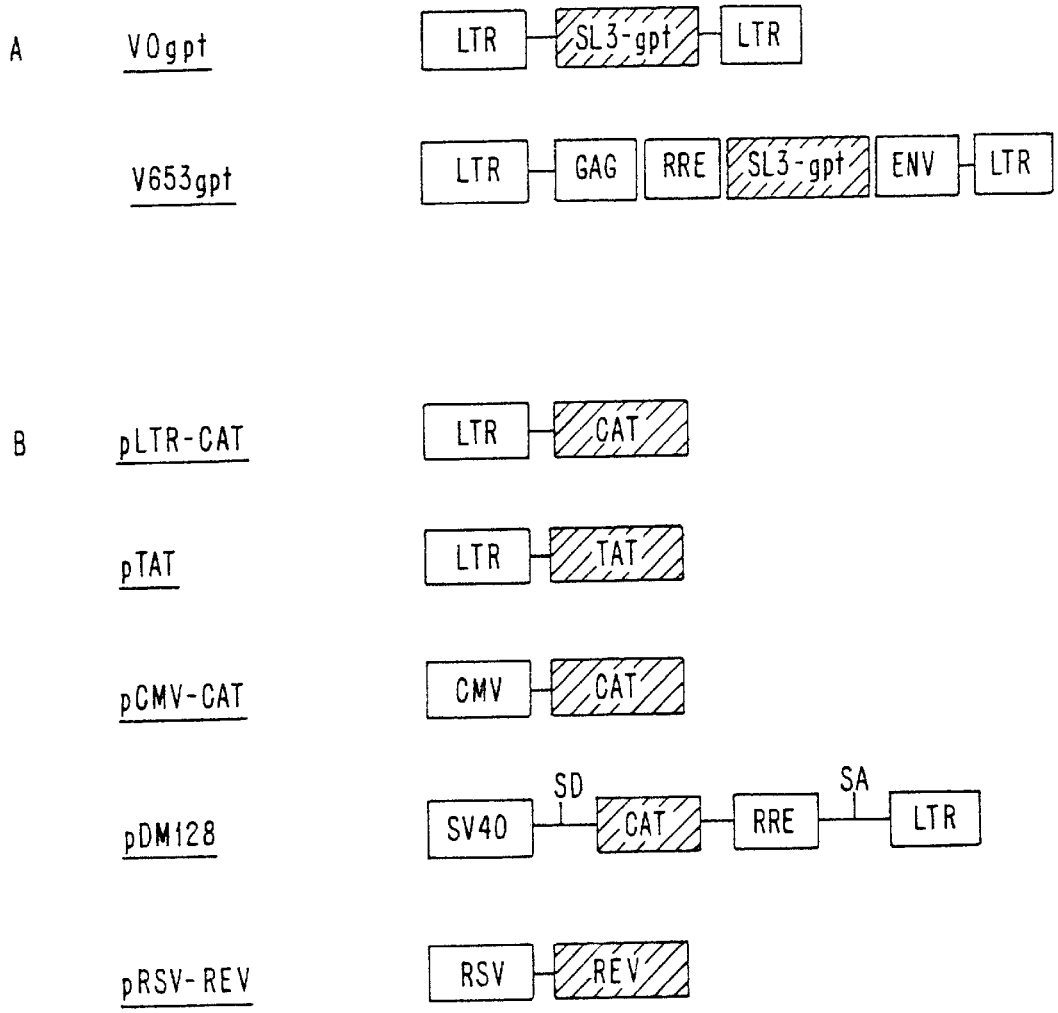
FIG. 8, panels A and B, provide schematic drawings of plasmids described in the examples.

As shown in FIG. 8, pLTR-CAT and pCMV-CAT plasmids contain the chloramphenicol acetyltransferase (CAT) reporter gene driven by an HIV-1 LTR and a cytomegalovirus (CMV) promoter, respectively. In pTAT, the tat gene is driven by an HIV-1 LTR. pRSV-REV contains the Rous sarcoma virus promoter, and the rev gene from HIV-1-BRU. pDM128, derived from the env region of HIV-1, contains the Simian Virus 40 promoter, the CAT gene and a fragment of HIV-1 env including RRE, both in an intron flanked by HIV-1 splice donor and acceptor sites.

CAT assays

Plasmids were transfected by electroporation at 12, 6, 12, 12, and 6 µg/ml for pLTR-CAT, pTAT, pCMV-CAT, pDM128, and pRSV-REV respectively. Four million Hela-T4 cells in 400 µl of RPMI1640-20% were mixed at 4° C. with the plasmids. After 10 min on ice, cells were electroporated at 250 V, and cultured in T25 flasks (Costar) containig 8 ml of DMEM-10% FCS. At day 3 post-electroporation, CAT production was determined by immunocapture on the cell lysate (CAT ELISA, Boehringer Mannheim, Indianapolis, Ind.). To determine the protein concentration, 8 µl of each cell lysate was mixed in a microtiter plate with 152 µl of water and 40 µl of Bradford protein assay dye reagent concentrate (Bio-Rad, Hercules, Calif.), and the absorbance was read at 570 nm. A standard curve was established using bovine immunoglobulins.

Cell transfection with HIV-1-MN

Cells were electroporated as described in the CAT assay, and the p24 production was monitored in the culture supernatant using an antigen capture assay (Coulter). The HIV-1-MN molecular clone has been described previously.

Anti-rev effect of the V653gpt vector

The HIV-1 vector V653gpt was used to transduce CD4+ cells. V653gpt contains the two HIV LTRs, a SL3-gpt cassette containing the selectable marker gene xanthine-guanine phosphoribosyl transferase (gpt), driven by an internal promotor, the murine retroviral LTR SL3, and three sequences involved in packaging: the major ψ sequence, a 5' portion of the gag gene, and a fragment of the env gene. This env fragment encompasses RRE. During wild-type HIV infection of a V653gpt-transduced cell, vector RRE sequences could have a decoy effect on neosynthesized rev proteins. To test this possibility, a functional assay to assess Rev function was performed. This assay uses a reporter plasmid, pDM128, which contains RRE and the CAT gene in an intron (FIG. 8, panel b). In the absence of rev, cells transfected with pDM128 express only cytoplasmic spliced transcripts and do not produce CAT protein. In the presence of rev, unspliced RNAs enter the cytoplasm, and CAT is synthesized. The amount of CAT produced by transduced or non-transduced cells was compared after cotransfection with the reporter gene, pDM128, and a plasmid encoding rev, pRSV-REV (FIG. 8, panel b). In addition, the cells were also transfected with the tat expression plasmid, pTAT, to induce the expression of RRE+ V653gpt transcripts. The rev-dependent production of the CAT molecule was reduced in V653gpt-transduced cells. To ensure that this impaired CAT production was not due to any constitutive defect of the V653gpt-transduced cells, a plasmid, pCMV-CAT, harboring the same reporter gene, CAT, but under the control of a CMV promoter was comparatively assessed. The expression of CAT after transfection with pCMV-CAT was similar in transduced and non-transduced Hela-T4 cells. Thus, V653gpt will interfere with the rev-RRE interaction necessary for viral constitutive proteins expression during HIV infection. It is noteworthy that for this vector, the RRE decoy expression is inducible, so that no toxic effect due to the sequestration of RRE-binding cellular factors is observed. Because of RRE, V653gpt will likely follow the rev-RRE export pathway from the nucleus to the cytoplasm, and thereby be localized with HIV RNA (FIG. 7). Such a colocalization is an advantage for a vector carrying an antiviral agent such as a ribozyme. Finally, V653gpt, which contains a 5'-fragment of the gag gene, which has additional anti-HIV effects. The truncated gag proteins it encodes associates with wild-type gag proteins and interferes with the proper formation of the viral core (a trans-dominant effect).

Transduction of CD4+ cells with a minimum HIV-1 vector

HIV vectors typically have both the 5'- and 3'-LTR. The presence of these regulatory sequences, particulary TAR, interferes with the HIV infection process in transduced cells. V653gpt is too complex for simple analysis of its TAR decoy effect on HIV infection. Therefore, a minimum vector, V0gpt was constructed as described. V0gpt includes the two HIV-1 LTRs, the packaging sequences located 5' of the ATG gag initiator, (i.e. the three first loops of the main packaging signal), and the SL3-gpt cassette. V0gpt was transfected into the HIV packaging cell line ψ-422. The supernatant of the stable cell lines obtained (gV0 lines) were checked for infectivity and for transduction capacity. The virions produced by these cell lines were non-infectious. Ten ng of p24 equivalent of gV0 virions did not induce any viral production after a 4-week culture in the presence of Molt4/8 CD4+ cells. In the same assay, wild-type HIV-1-MN tissue culture infectious dose 50% (TCID50) was $10^{-3}$ ng (Table 1). Yet, gV0 virions were able to transduce Hela-T4 cells—and not Hela cells—with a titer ranging from 1.2 to $2.0 \times 10^3$ transducing units (TU) per milliliter of supernatant (Table 1). The integrity of the vector in gene altered cells was controlled by Southern blot. Of note, the transduction efficiencies we obtained here with V0gpt are lower than those (e.g., roughly $10^5$ TU/ml) obtained using V653gpt. Th difference between the two vectors is due to the fact that V653gpt contains two sequences in addition to the main packaging signal Y (the 5' portion of gag, and the RRE-encompassing fragment of env) known to be involved in HIV RNA packaging, and is, therefore, packaged more efficiently than V0gpt.

Anti-tat effect of the V0gpt vector

To examine a TAR decoy effect of V0gpt on tat during the infection of V0gpt-transduced cells, the reporter plasmid pLTR-CAT, and a tat expression vector, pTAT were used. The amount of CAT protein produced by transduced and non-transduced Hela-T4 cells after transient transfection with both plasmids. In 3 independent experiments, the amount of CAT protein produced by V0gpt-transduced cells under tat transactivation was reduced. As a positive control, the same cells were transfected with pCMV-CAT. The production of CAT was the same for the two types of cells, with or without V0gpt-transduction. This implied that, in addition to a TAR decoy effect on the viral tat transactivator, the vector LTR also had a decoy effect on other viral transcription activators, i.e. the constitutive and inducible cellular DNA-binding proteins involved in HIV activation.

The TAR decoy effect on HIV expression was also assessed. Hela-T4 cells, transduced with V0gpt or untransduced controls, were transfected with a wild-type HIV-1-MN clone, and viral production was monitored. With two different HIV molecular clone concentrations, a reduction in p24 expression by V0gpt transduced cells, as compared with non-transduced cells was observed. Thus, TAR decoy effects shown for V0gpt were responsible for inhibition of HIV expression in transduced cells. Anti-viral agents such as anti-HIVribozymes add to this inhibitory effect.

All publications and patent applications cited in this specification are herein incorporated by reference as if each individual publication or patent application were specifically and individually indicated to be incorporated by reference in its entirety for all purposes. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. A cell transformation vector comprising a first HIV LTR, a second HIV LTR, and an HIV-2 packaging site nucleic acid between the two HIV LTRs and an HIV-1 gag protein, wherein at least one of the HIV LTRs is an HIV-2 LTR from HIV-2$^{KR}$.

2. The vector of claim 1, wherein the vector further comprises a transcription cassette, which transcription cassette comprises a heterologous promoter which directs expression of a nucleic acid of interest, and further wherein the transcription cassette is located in one of the HIV LTRs.

3. The vector of claim 2, wherein the nucleic acid of interest encodes a ribozyme which specifically cleaves an HIV nucleic acid.

4. The vector of claim 3, wherein the promoter is a pol III promoter.

5. The vector of claim 4, wherein the first HIV LTR is an HIV-2$^{KR}$ 5'LTR and the second HIV LTR is an HIV-2$^{KR}$ 3'LTR.

6. A method of transforming a cell in vitro, comprising contacting the cell with the vector of claim 1.

7. The method of claim 6, wherein the method further comprises isolating the cell from a mammal prior to contacting the cell with the vector.

8. The method of claim 6, wherein the cell is a CD34$^+$ stem cell.

9. A cell transformation vector comprising a first HIV LTR, a second HIV LTR, and an HIV-2 packaging site nucleic acid between the two HIV LTRs and an HIV-1 gag protein, wherein the vector further comprises an MPMV nucleic acid nuclear export subsequence.

10. The vector of claim 9, wherein the vector further comprises a transcription cassette, which transcription cassette comprises a heterologous promoter which directs expression of a nucleic acid of interest, and further wherein the transcription cassette is located in one of the HIV LTRs.

11. The vector of claim 10, wherein the nucleic acid of interest encodes a ribozyme which specifically cleaves an HIV nucleic acid.

12. The vector of claim 11, wherein the promoter is a pol III promoter.

13. The vector of claim 12, wherein the first HIV LTR is an HIV-2 5'LTR and the second HIV LTR is an HIV-2 3'LTR.

14. A method of transforming a cell in vitro, comprising contacting the cell with the vector of claim 9.

15. The method of claim 14, wherein the method further comprises isolating the cell from a mammal prior to contacting the cell with the vector.

16. The method of claim 15, wherein the cell is a CD34$^+$ stem cell.

17. A cell transformation vector comprising a first HIV LTR, a second HIV LTR, and an HIV-2 packaging site nucleic acid between the two HIV LTRs and an HIV-1 gag protein, wherein the vector further comprises a transcription cassette, which transcription cassette comprises a heterologous promoter which directs expression of a nucleic acid of interest, and further wherein the transcription cassette is located in one of the HIV LTRs.

18. The vector of claim 17, wherein the transcription cassette is located in the first HIV LTR, and wherein the vector further comprises a second transcription cassette located in the second HIV LTR.

19. The vector of claim 18, wherein the vector further comprises a third transcription cassette located between the first HIV LTR and the second HIV LTR.

20. The vector of claim 17, wherein the nucleic acid of interest encodes a ribozyme which specifically cleaves an HIV nucleic acid.

21. The vector of claim 17, wherein the promoter is a pol III promoter.

22. The vector of claim 17, wherein the promoter is a t-RNAval promoter.

23. The vector of claim 17, wherein the first HIV LTR is an HIV 5'LTR and the second HIV LTR is an HIV 3'LTR.

24. The vector of claim 23, wherein the HIV 5'LTR is an HIV-2 5'LTR and the HIV 3'LTR is an HIV-2 3'LTR.

25. The vector of claim 17, wherein the transcription cassette is located in a U3 region of at least one of the HIV LTRs.

26. The vector of claim 25, wherein the transcription cassette is located in a U3 region of the second HIV LTR which is an HIV-2 3'LTR.

27. The vector of claim 17, wherein the vector further comprises a VSV envelope protein.

28. The vector of claim 17, wherein at least one of the HIV LTRs is an HIV-2 LTR.

29. A method of transforming a cell in vitro, comprising contacting the cell with the vector of claim 17.

30. The method of claim 29, wherein the method further comprises isolating the cell from a mammal prior to contacting the cell with the vector.

31. The method of claim 29, wherein the cell is a CD34$^+$ stem cell.

32. The method of claim 29, wherein the nucleic acid of interest encodes a ribozyme which specifically cleaves an HIV nucleic acid and wherein transforming the cell with the vector renders the cell resistant to HIV infection.

33. A cell transformation vector comprising an HIV 5'LTR, an HIV 3'LTR, and an HIV-2 packaging site nucleic acid between the two HIV LTRs, and viral particles comprising an HIV-1 gag protein, an env protein, and an HIV-1 vpr protein, wherein the HIV-1 gag protein is a p25 subproduct.

34. The vector of claim 33, wherein the HIV 5'LTR is an HIV-2 5'LTR and the HIV 3'LTR is an HIV-2 3'LTR.

35. The vector of claim 34, wherein the vector further comprises a transcription cassette, which transcription cassette comprises a heterologous promoter which directs expression of a nucleic acid of interest, and further wherein the transcription cassette is located in one of the HIV LTRs.

36. The vector of claim 35, wherein the nucleic acid of interest encodes a ribozyme which specifically cleaves an HIV nucleic acid.

37. The vector of claim 36, wherein the promoter is a pol III promoter.

38. The vector of claim 33, wherein the vector further comprises a VSV envelope protein.

39. A method of transforming a cell in vitro, comprising contacting the cell with the vector of claim 33.

40. The method of claim 39, wherein the method further comprises isolating the cell from a mammal prior to contacting the cell with the vector.

41. The method of claim 40, wherein the cell is a $CD34^+$ stem cell.

* * * * *